(12) United States Patent
Tanaka et al.

(10) Patent No.: US 7,732,761 B2
(45) Date of Patent: Jun. 8, 2010

(54) METHOD FOR MEASURING A PATTERN DIMENSION USING A SCANNING ELECTRON MICROSCOPE

(75) Inventors: Maki Tanaka, Yokohama (JP); Chie Shishido, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 271 days.

(21) Appl. No.: 11/673,057

(22) Filed: Feb. 9, 2007

(65) Prior Publication Data

US 2007/0187595 A1 Aug. 16, 2007

(30) Foreign Application Priority Data

Feb. 16, 2006 (JP) ............................. 2006-038945

(51) Int. Cl.
| G06F 7/60 | (2006.01) |
| G06F 17/10 | (2006.01) |
| G06F 17/50 | (2006.01) |
| G06G 7/48 | (2006.01) |
| G01N 23/00 | (2006.01) |
| G21K 7/00 | (2006.01) |
| G06G 7/62 | (2006.01) |

(52) U.S. Cl. ....................... 250/307; 250/306; 250/310; 250/311; 703/2; 703/6; 703/13

(58) Field of Classification Search ................. 250/306, 250/307, 310, 311, 492.1, 492.3; 703/6, 703/13, 2

See application file for complete search history.

(56) References Cited

U.S. PATENT DOCUMENTS 3,585,382 A * 6/1971 Suganuma .................. 250/310

(Continued)

FOREIGN PATENT DOCUMENTS

JP 11-316115 11/1999

(Continued)

OTHER PUBLICATIONS

J.S. Villarrubia et al, "Scanning electron microscope analog of scatterometry", Proc. SPIE 4689, pp. 304-312 (2002).

(Continued)

*Primary Examiner*—Jack I Berman
*Assistant Examiner*—Brooke Purinton
(74) *Attorney, Agent, or Firm*—Antonelli, Terry, Stout & Kraus, LLP.

(57) ABSTRACT

To provide a consistent, high-speed, high-precision measurement method based on an electron beam simulation by reflecting the apparatus characteristics of a CD-SEM in an electron beam simulation, the present invention discloses a method for measuring a measurement target pattern with a CD-SEM, the method comprising the steps of performing an electron beam simulation on various target pattern shapes, which is reflected apparatus characteristic and image acquisition conditions; creating SEM simulated waveforms; storing a combination of the created SEM simulated waveforms and pattern shape information corresponding to the created SEM simulated waveforms as a library; comparing an acquired actual electron microscope image with the SEM simulated waveforms; selecting the SEM simulated waveform that is most similar to the actual electron microscope image; and estimating the shape of the measurement target pattern from the pattern shape information corresponding to the selected SEM simulated waveform.

13 Claims, 17 Drawing Sheets

U.S. PATENT DOCUMENTS

| | | | | |
|---|---|---|---|---|
| 4,943,722 | A | * | 7/1990 | Breton et al. ............... 250/310 |
| 5,719,796 | A | * | 2/1998 | Chen ........................... 703/13 |
| 7,305,333 | B2 | * | 12/2007 | Stanton ........................ 703/2 |
| 2004/0225488 | A1 | * | 11/2004 | Wang et al. .................... 703/22 |
| 2005/0173633 | A1 | * | 8/2005 | Tanaka et al. ............... 250/311 |
| 2005/0221207 | A1 | * | 10/2005 | Nagatomo et al. ....... 250/492.3 |
| 2005/0253083 | A1 | * | 11/2005 | Sato et al. ................... 250/398 |
| 2008/0249754 | A1 | * | 10/2008 | Niu et al. ........................ 703/6 |

FOREIGN PATENT DOCUMENTS

| | | |
|---|---|---|
| JP | 2000-067797 | 3/2000 |
| JP | 2003-142021 | 5/2003 |

OTHER PUBLICATIONS

J.S. Villarrubia, et al "A simulation study of repeatability and bias in the CD-SEM," Proc. SPIE 5038, pp. 138-149, 2003.

Tanaka et al, "Influence of Focus Variation on Linewidth Measurements", Proc. SPIE 5752, pp. 144-155 (2005).

JR. Lowney, "Monte Carlo Simulation Of Scanning Electron Microscope Signals For Lithographic Metrology," Scanning vol. 18, pp. 301-306 (1996).

D.C. Joy, Monte Carlo Modeling For Electron Microscopy And Microanalysis, Oxford University Press 1995.

D.C. Joy et al, "Metrics of resolution and performance for CD-SEMs", Proc. SPIE 3998, pp. 108-114 (2000).

Sato et al, "A Method for calculating the current density of charged particle beams and the effect of finite source size and spherical and chromatic aberrations on the focusing characteristics," J. Vac. Sci. Technol. B9(5), Sep./Oct. 1991.

P.B. Kenway et al, "Electron density distributions in spherically aberrated probes, "Inst. Phys. Conf. Ser. No. 68, Chapter 3 1983.

* cited by examiner

IMAGE A

IMAGES B AND C

108
Img-s-A(x-xsA, tool-A, sample0)

109
Img-s-B(x-xsB, tool-B, sample0)

106
Img-A(x)

107
Img-B(x)

METHOD FOR MEASURING A PATTERN DIMENSION USING A SCANNING ELECTRON MICROSCOPE

BACKGROUND OF THE INVENTION

The present invention relates to a method and system for evaluating the shape of a circuit pattern, which is formed on a wafer during a semiconductor manufacturing process, by using an electron microscope image of the circuit pattern, which is obtained by an electron microscope, and more particularly to a method for measuring a measurement target pattern with an electron microscope.

In a semiconductor wafer manufacturing process, a multilayer pattern formed on a wafer has been rapidly rendered microscopic. Therefore, process monitoring for checking whether the pattern is formed on the wafer in compliance with design specifications has become increasingly important. The wiring widths of transistor gate wiring patterns and other similar wiring patterns are significantly associated with device performance. Therefore, it is particularly important that a wiring manufacturing process for such wiring patterns be properly monitored.

A critical dimension scanning electron microscope (CD-SEM), which is capable of picking up a wiring image at magnifications of 100000× to 200000×, has been conventionally used as a tool for measuring the wiring width of a microscopic wiring on the order of several tens of nanometers.

An example of a length measurement process performed with a scanning electron microscope is described in Japanese Patent JP-A No. 316115/1999. The process disclosed by Japanese Patent JP-A No. 316115/1999 examines a local region within an image of a measurement target wiring, creates a projection profile by averaging a wiring signal profile in a longitudinal direction of wiring, and calculates a wiring dimension as the distance between right- and left-hand wiring edges detected in the created profile.

However, as disclosed by J. S. Villarrubia, A. E. Vladar, J. R. Lowney, and M. T. Postek, "Scanning electron microscope analog of scatterometry," Proc. SPIE 4689, pp. 304-312 (2002) (hereinafter referred to Proc. SPIE 4689), the SEM signal waveform changes in accordance with a change in the shape of a target pattern to be measured. This causes a measurement error. As semiconductor patterns are becoming increasingly microscopic, the influence of such a measurement error on process monitoring is becoming greater. A method for reducing such a measurement error is disclosed by J. S. Villarrubia, A. E. Vladar, and M. T. Postek, "A simulation study of repeatability and bias in the CD-SEM," Proc. SPIE 5038, pp. 138-149, 2003 (hereinafter referred to as Proc. SPIE 5038). This method performs a simulation in advance to calculate the relationship between a pattern shape and SEM signal waveform and uses the obtained calculation results to make high-precision measurements that are not dependent on a target shape.

SUMMARY OF THE INVENTION

As described in conjunction with the above background art, a measurement error dependent on the shape of a target pattern occurs when the dimensions of a semiconductor pattern are measured with a CD-SEM. On the other hand, the methods disclosed by Proc. SPIE 4689 and Proc. SPIE 5038 perform a simulation in advance to calculate the relationship between the pattern shape and SEM signal waveform and uses the obtained calculation results to make high-precision measurements that are not dependent on a target shape. These measurement methods are hereinafter referred to as model-based measurement methods. When the model-based measurement methods are used to make consistent, high-precision measurements, it is important that a simulation be performed with high accuracy.

However, the SEM signal waveform varies with apparatus characteristics as disclosed by Japanese Patent JP-A No. 67797/2000. Therefore, it is necessary to consider such apparatus characteristics when the above-mentioned art is used to perform a simulation. The methods disclosed by Proc. SPIE 4689 and Proc. SPIE 5038 use some apparatus parameters during a simulation. However, the apparatus parameters are estimated when a matching procedure is performed in relation to an actual waveform. Therefore, inconsistent results may be produced as described by M. Tanaka, J. S. Villarrubia, and A. E. Vladar, "Influence of Focus Variation on Linewidth Measurements," Proc. SPIE 5752, pp. 144-155 (2005) (hereinafter referred to as Proc. SPIE 5752). Further, apparatus parameter estimation takes a large amount of processing time.

The present invention provides a consistent, high-speed, high-precision measurement method based on the use of an electron beam simulation (Monte Carlo simulation) by performing an electron beam simulation which is reflected (considered) the apparatus characteristics of an electron microscope (CD-SEM).

In accordance with predicted values of shapes and dimensional changes of a measurement target sample, the present invention performs an electron beam simulation to create SEM images for cases where these shape changes are generated, and records (stores) simulation images of various shapes as a library. Here, the term "simulation" indicates to a general method for simulating a physical phenomenon on the basis of a model. In the present invention, an electron beam simulation for library creation especially indicates simulating a process of electron microscope image creation in an SEM and calculating the relationship between a measurement target shape and electron microscope image waveform. The electron beam simulation for library creation does not produce correct results if an inappropriate model is used. When the electron beam simulation for library creation is to be conducted, the present invention enhances the accuracy of electron beam simulation and measurements based on electron beam simulation by providing means for properly setting up the characteristics of an apparatus that acquires an electron microscope image. In this instance, various apparatus characteristic parameters (electron optics resolution, beam divergence half angle, aberration coefficients, etc.) used for the electron beam simulation are the design information about electron optics, the values calculated in accordance with the design information, or the values obtained in advance by measuring actual apparatus characteristic with measurement means. When measurements are to be made, an SEM image of a measurement target pattern is picked up and compared with various SEM waveforms recorded (stored) in a prepared library (a first simulated waveform or a second simulated waveform, which is created when the first simulated waveform is subjected to interpolation, Gaussian filtering, or the like), to select the most similar SEM waveform. This makes it possible to make high-precision measurements while considering a three-dimensional shape.

According to one aspect of the present invention, a method is provided for measuring a measurement target pattern with an electron microscope to acquire an actual electron microscope image of the measurement target pattern under image acquisition conditions and estimate the shape of the measurement target pattern by using the acquired actual electron microscope image, the method comprising: a measurement recipe creation step of obtaining pattern shape information by modeling approximate shapes of various target patterns in numerical data in advance, which are obtained by varying dimensions in a predetermined predicted variation range; a library creation step of creating first simulated waveforms of electron microscope signals concerning various target pattern shapes by performing an electron beam simulations (Monte Carlo simulations) on the various target pattern shapes within the predicted variation range, the electron beam simulations being reflected apparatus characteristic of the electron microscope and image acquisition condition imposed by the electron microscope, and storing a combination of the created first simulated waveforms of the electron microscope signals and pattern shape information, which corresponds to the first simulated waveforms and are obtained in the measurement recipe creation step, as a library (in a form of a library); and a measurement step of selecting a first simulated waveform or a second simulated waveform which is most similar waveform to the actual electron microscope image by comparing the acquired actual electron microscope image with the first simulated waveforms of the electron microscope image created in the library creation step, or second simulated waveforms which are created from the first simulated waveforms, and estimating the shape of the measurement target pattern from the pattern shape information (pattern edge position information included) that corresponds to the selected first simulated waveform or second simulated waveform and is used in the library creation step.

According to another aspect of the present invention, the method is provided for measuring a measurement target pattern with an electron microscope, wherein in the library creation step, the apparatus characteristic of the electron microscope is any one of an electron optics resolution, beam shape, beam divergence half angle, or aberration coefficients, or a combination of two or more of these.

According to another aspect of the present invention, the method is provided for measuring a measurement target pattern with an electron microscope, wherein in the library creation step, the any one of the electron optics resolution, beam shape, beam divergence half angle, or aberration coefficients, or the combination of two or more of these being the apparatus characteristic of the electron microscope reflected in the electron beam simulation, is determined by using design information about the electron microscope (electron optics).

According to another aspect of the present invention, the method is provided for measuring a measurement target pattern with an electron microscope, wherein in the library creation step, the any one of the electron optics resolution, beam shape, beam divergence half angle, or aberration coefficients, or the combination of two or more of these being the apparatus characteristics of the electron microscope reflected in the electron beam simulation, is determined based on measurement results measured by measurement means to determine According to another aspect of the present invention, the method is provided for measuring a measurement target pattern with an electron microscope, wherein the library creation step includes the steps of storing the apparatus characteristic of the electron microscope for each apparatus of the electron microscope, and reflecting the apparatus characteristic in the electron beam simulation, which is obtained by reading the apparatus characteristics stored for each apparatus of the electron microscope when the first simulated waveform is to be created.

According to another aspect of the present invention, the method is provided for measuring a measurement target pattern with an electron microscope, wherein the library creation step includes the steps of storing the apparatus characteristic of the electron microscope for each set of the image acquisition conditions including at least electron beam landing energy (accelerating voltage) and pixel size, and reflecting the apparatus characteristic in the electron beam simulation by reading the apparatus characteristic stored for each set of the image acquisition conditions when the first simulated waveform is to be created.

According to another aspect of the present invention, the method is provided for measuring a measurement target pattern with an electron microscope, wherein the library creation step includes the steps of calculating a best focus position by using simulation images for each of the target pattern shapes in the same evaluation method as with an actual electron microscope, and reflecting the calculated best focus position in the electron beam simulation as an image acquisition condition imposed by the electron microscope.

According to another aspect of the present invention, there is provided a method for measuring a measurement target pattern with an electron microscope to acquire actual electron microscope images of the measurement target pattern with electron beams at two or more different incident angles under image acquisition conditions and estimate the three-dimensional shape of the measurement target pattern by using the acquired two or more actual electron microscope images, the method comprising: a measurement recipe creation step of obtaining pattern shape information by modeling approximate shapes of various target patterns in numerical data in advance, which are obtained by varying dimensions in a predetermined predicted variation range; a library creation step of creating a group of first simulated waveforms of electron microscope signals obtained by irradiating the various target pattern shapes with the electron beams at the two or more different incident angles by performing electron beam simulations on the various target pattern shapes within the predicted variation range, the electron beam simulations being reflected the apparatus characteristic of the electron microscope and image acquisition conditions imposed by the electron microscope, including conditions for emitting electron beams at the two or more different incident angles, and storing a combination of the created group of the two or more first simulated waveforms of the electron microscope signals and the pattern shape information, which corresponds to the created group of the first simulated waveforms and is obtained in the measurement recipe creation step, as a library (in a form of a library); and a measurement step of calculating measurement target pattern edge positions within each of the actual electron microscope images by comparing the acquired two or more actual electron microscope images with the group of the first simulated waveforms created in the library creation step or a group of second simulated waveforms, which are created from the group of the first simulated waveforms, and measuring the three-dimensional shape of the measurement target pattern from a combination of the calculated measurement target pattern edge positions within the actual electron microscope images.

According to still another aspect of the present invention, a method is provided for measuring a measurement target pattern with an electron microscope to acquire actual electron microscope images of the measurement target pattern with electron beams at two or more different incident angles under image acquisition conditions and estimate the three-dimensional shape of the measurement target pattern by using the acquired two or more actual electron microscope images, the method comprising: a measurement recipe creation step of obtaining pattern shape information by modeling approximate shapes of various target patterns in numerical data in advance, which are obtained by varying dimensions in a predetermined predicted variation range; a library creation step of creating a group of first simulated waveforms of electron microscope signals obtained by irradiating the various target pattern shapes with the electron beams at the two or more different incident angles by performing electron beam simulations on the various target pattern shapes within the predicted variation range, the electron beam simulations being reflected apparatus characteristic of the electron microscope and image acquisition conditions imposed by the electron microscope, including conditions for emitting electron beams at the two or more different incident angles, and storing a combination of the created group of the two or more first simulated waveforms of the electron microscope signals and the pattern shape information, which corresponds to the created group o the first simulated waveforms and is obtained in the measurement recipe creation step, as a library; and a measurement step of comparing the acquired two or more actual electron microscope images with the group of the first simulated waveforms created in the library creation step or a group of second simulated waveforms, which are created from the group of the first simulated waveforms, and measuring the three-dimensional shape of the measurement target pattern by selecting the pattern shape information in which the total errors between the two or more actual electron microscope images and the group of the first simulated waveforms or the group of the second simulated waveforms is minimum.

As described above, the present invention can reduce the number of parameters to be estimated because it predetermines some or all of the apparatus parameters of the electron microscope in accordance with design values or measured values, instead of estimating by nonlinear least-square method. When the nonlinear least-squares method is used, the time required for estimation increases with an increase in the number of parameters to be estimated. If similar signal waveforms are given with a certain number of parameter combinations, the results might not converge. If a large number of parameters are involved, the estimation accuracy for each parameter may decrease due to noise, thereby degrading measurement repeatability.

In other words, the present invention can avoid vagueness in parameter estimation because it predetermines the apparatus parameters of the electron microscope by another method. Therefore, the present invention makes it possible to make stable, high-speed CD-SEM measurements.

The present invention can decrease the number of parameters to be estimated during the use of a model-based measurement method. Therefore, the present invention makes it possible to achieve consistent estimation and reduce the calculation time required for measurement.

Further, the present invention provides enhanced electron beam simulation accuracy by reflecting the apparatus characteristics of the CD-SEM in electron beam simulation. As a result, the accuracy of the model-based measurement method is also improved.

Furthermore, the present invention determines the apparatus characteristics of the CD-SEM in accordance with electron optics design values or predetermines the apparatus characteristic by allowing measurement means to make measurements, and reflects the determined apparatus characteristic in electron beam simulation. Therefore, the present invention also makes it possible to reduce measurement variations among a plurality of or CD-SEMs.

These and other objects, features, and advantages of the invention will be apparent from the following more particular description of preferred embodiments of the invention, as illustrated in the accompanying drawings.

DETAILED DESCRIPTION OF THE PREFERRED EMBODIMENTS

Embodiments of a method and apparatus or system for measuring a measurement target pattern with an electron microscope according to the present invention will now be described with reference to the accompanying drawings.

First Embodiment (Providing Increased Accuracy by Reflecting Apparatus Characteristics: Library Creation Procedure)

A first embodiment of the method and apparatus (system) for measuring a measurement target pattern according to the present invention will now be described by explaining about a basic procedure and system configuration for the use of a CD-SEM with reference to FIGS. 1 to 6.

Figure 1A:
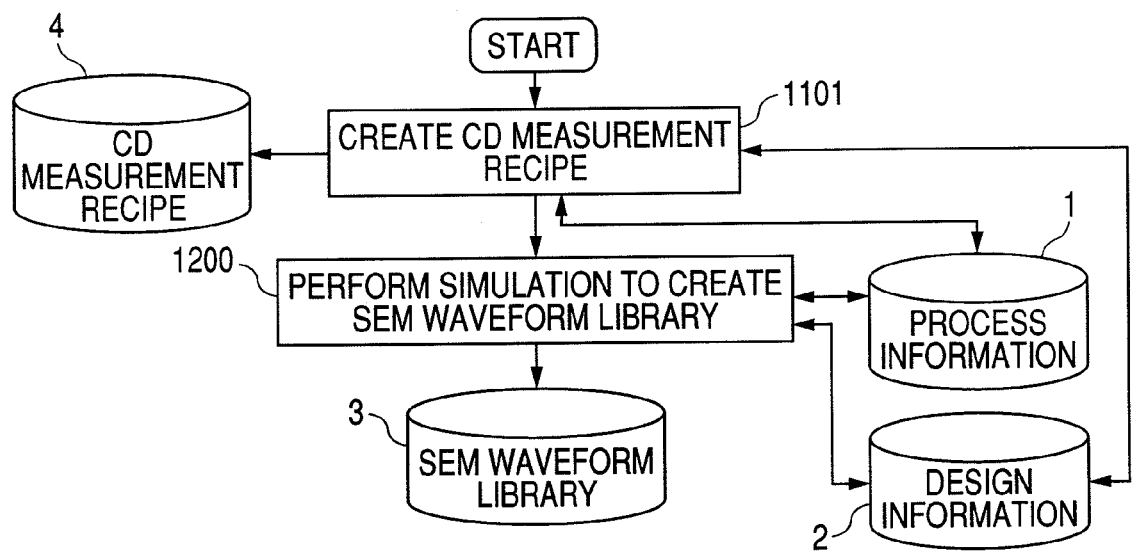
FIG. 1A illustrates a system configuration that is used to generate a simulation waveform for allowing an SEM measurement apparatus to measure a measurement target pattern.
Figure 1B:
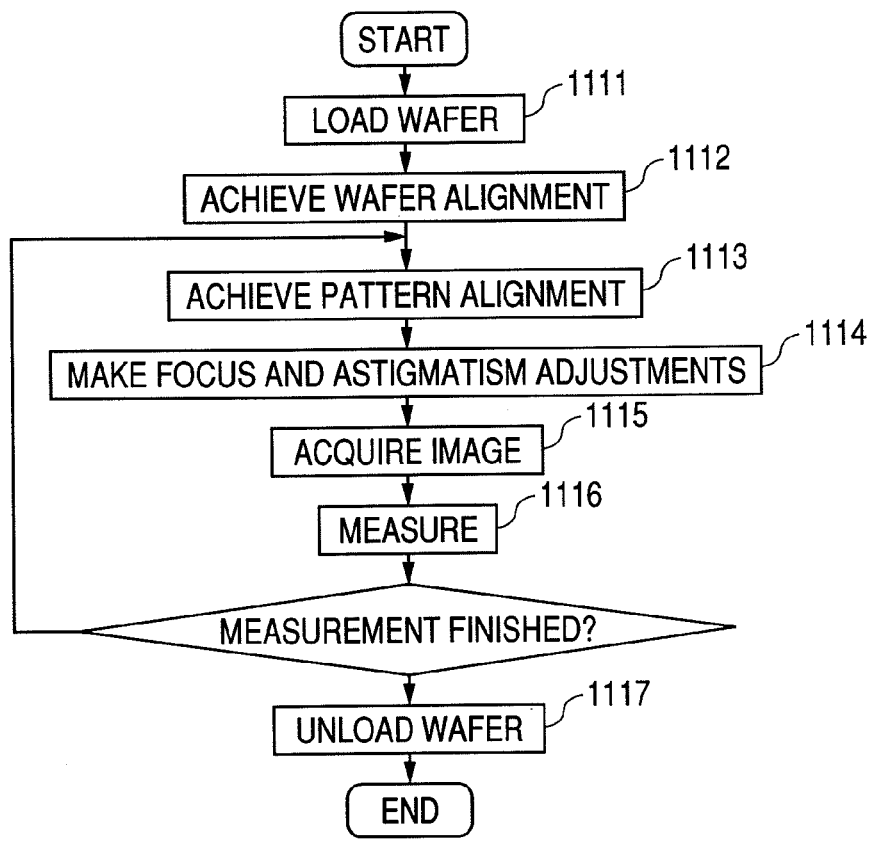
FIG. 1B is a flowchart illustrating a procedure for measuring the measurement target pattern.

FIG. 1A shows an embodiment of a procedure for creating a CD measurement recipe 4 and SEM waveform library 3 for image acquisition, which are used by the method and apparatus (system) for measuring a pattern according to the present invention. FIG. 1B shows an embodiment of a procedure for making actual measurements.

Figure 4:
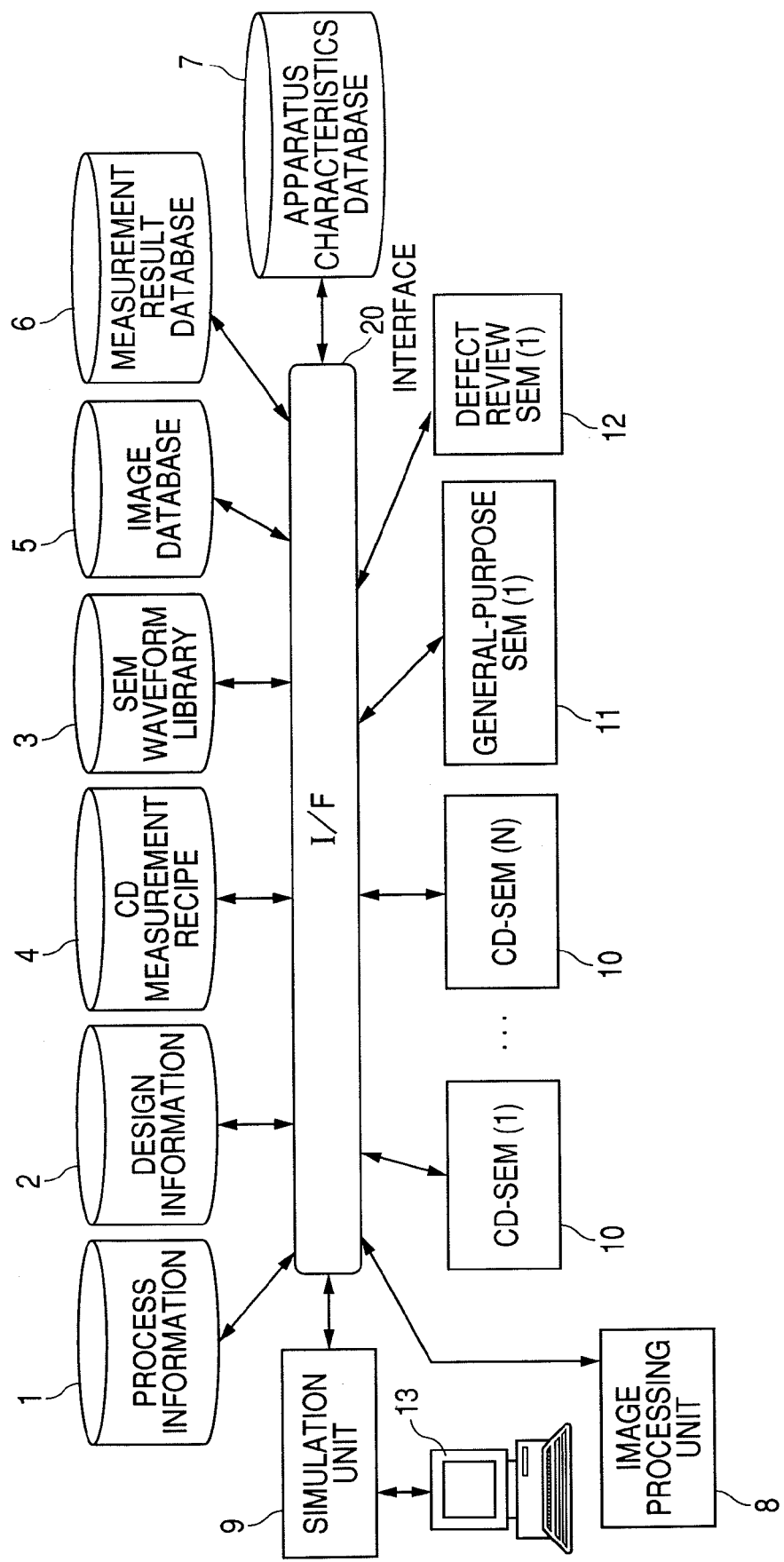
FIG. 4 is a schematic block diagram illustrating an embodiment of a pattern measurement system.

A processing/control section 300 of a CD-SEM 10, which is shown in FIG. 4, or a CD measurement recipe creation section (not shown), which is installed in a different computer connected via an interface (network) 20, first creates a CE measurement recipe as shown in FIG. 1A (step 1101) by using measurement target pattern information that is derived from process information 1 and design information 2 and necessary for measurement recipe creation, as is the case with a normal CD-SEM. The information necessary for CD measurement recipe creation includes the product name and the manufacturing process name of a measurement target pattern, which are derived from the process information 1, and the position of the measurement target pattern on a wafer, the type of the pattern (line pattern, hole pattern, or other pattern), and the design dimensions of the pattern, which are derived, for instance, from the design information 2.

The CD measurement recipe 4 created in a CD measurement recipe creation step (step 1101) according to the present invention contains a record of information necessary to acquire an image of a measurement target, such as alignment pattern information, measurement target pattern position and image acquisition conditions (tools) such as pixel size (image magnification), SEM beam (prove) current and SEM landing energy (accelerating voltage) etc. The image of the measurement target pattern can be automatically taken measurement when the recipe is assigned by using a GUI (Graphical User Interface) or the like for a display connected in the CD-SEM apparatus, which is described later, or in a CD measurement recipe creation section (not shown). The above-mentioned information is recorded in a CD measurement recipe database 4. The recipe creation step (step 1101) may be performed by a CD-SEM main body 10, which is described later, or by a computer (CD recipe creation section) or other device that is separate from the CD-SEM apparatus and connected to the network 20. When the CD recipe creation section is furnished in this manner, it can be shared by the CD-SEM apparatus 10. If the measurement target pattern manufacturing process information 1 and design information 2 such as design data or the like are available, the CD measurement recipe 4 can be created with relative ease without using the actual CD-SEM apparatus and a wafer.

Figure 2A:
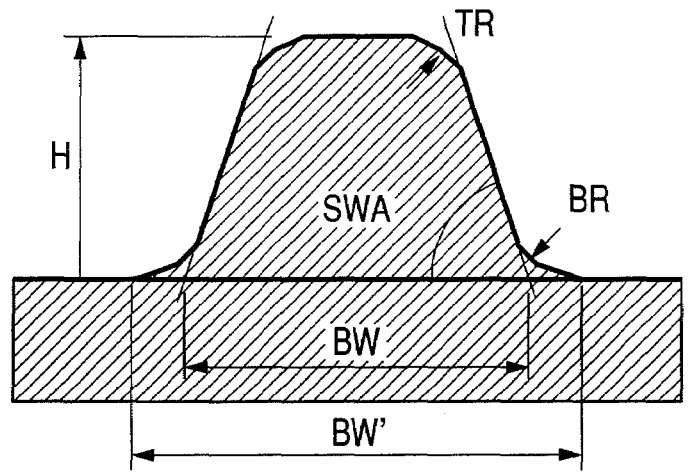
FIG. 2A shows a measurement target shape model.
Figure 2B:
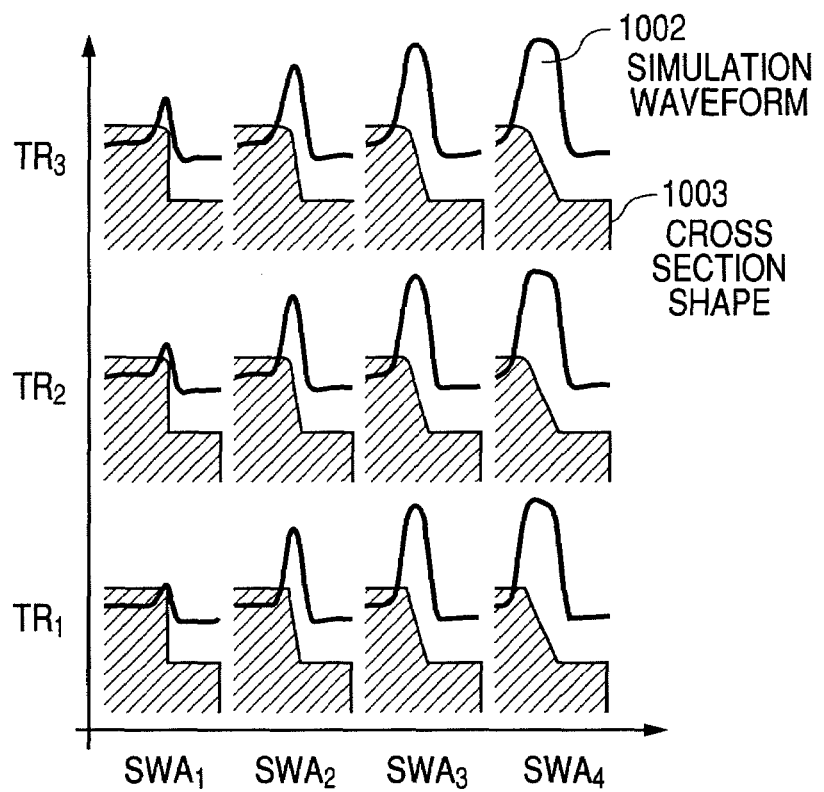
FIG. 2B illustrates a diagram to explain a simulation library.

After the CD measurement recipe 4 is created, for example, an electron beam simulation unit 9 which is shown in FIG. 4 performs an electron beam simulation (Monte Carlo simulation) to create the SEM image library 3 for use in pattern measurement according to the present invention in accordance with the information about the determined measurement target pattern (step 1200). For the SEM waveform library 3, for example, a reference cross section shape shown in FIG. 2A is created in advance. The SEM waveform library 3 changes various shape parameters (H, BW, TR, BR, SWA, etc.) shown in the figure as needed to match a range (predicted variation range) over which the measurement target actually varies with manufacturing process variations, and uses the resulting changed shape parameters. The parameters indicated in conjunction with the embodiment shown in FIG. 2A are H (line pattern height), BW (bottom width), TR (top corner round), BR (bottom corner round), and SWA (sidewall angle). The bottom width (BW) is a dimension that prevails when the bottom corner round is 0. However, the bottom width (BW') that includes a corner round may also be used. When the parameters BR and BW are known, the parameter BW' can be calculated with ease. The SEM waveform signals for the shapes determined as described above are calculated by performing an electron beam simulation, and combinations of input target cross section shapes and calculated SEM waveform signals are recorded in the library 3. FIG. 2B shows an example of data that is actually recorded in the library 3. In the example shown in FIG. 2B, the sidewall angle (SWA) and top corner round (TR) are varied as the elements of a measurement target pattern shape (cross section shape) 1003. The parameters to be varied should be determined to achieve an intended purpose. When, for instance, the measurement target pattern is an etched wiring pattern, the top corner round and pattern height do not significantly vary. Therefore, they can be fixed at appropriate values to reduce the number of parameters to be estimated and shorten the time required for calculation. In the case of gate wiring etching, on the other hand, the wiring width (including the average wiring width in addition to the bottom width), sidewall angle, and bottom corner round are important parameters that affect device performance. It is therefore important that they be accurately measured. As regards a developed photoresist pattern, the top corner round, sidewall angle, and measurement target height, which readily vary and are important for monitoring a status of stepper/scanner, should be varied within appropriate ranges to perform an electron beam simulation. When the shape parameters important for the process are varied as the measurement target parameters as described above to create the library 3 while fixing the parameters that do not vary in the process, high-sensitivity measurements can be made with the required calculation time minimized.

As shown in FIG. 2B, the shape and signal amount of a simulation waveform 1002 vary when the cross section shape 1003 varies. In the actual library 3, as shown in the figure for explanation purposes, these data sets constitute a collection of numerical data that is a combination of pattern cross section shape information expressed by the shape parameters shown in FIG. 2A (pattern shape information obtained by modeling numerical data of various approximate target pattern shapes within a predetermined predicted variation range) and signal amounts prevailing at various points corresponding to the cross section shapes calculated during an electron beam simulation.

In the present invention, the characteristics of a measuring apparatus (CD-SEM) are reflected in the electron beam simulation recorded in the library 3. A method for creating the cross section shape data to be input will be described in detail in conjunction with a second embodiment.

The library 3, which records the relationship between the above-mentioned cross section shapes and SEM signal waveforms, is recorded together with a combination of conditions that affect SEM image waveforms. For example, one library set is created for a combination of the measurement target pattern (product, process, and pattern position within chip layout) (sample), SEM image acquisition apparatus ID, and SEM image acquisition conditions (e.g., irradiation electron beam landing energy (accelerating voltage), pixel size (image magnification), beam scan speed, probe current, and retarding voltage (when a retarding electrode is used) etc. This library set is used to make actual measurements in a sequence that is indicated in FIG. 1B. First of all, a wafer is loaded into the CD-SEM apparatus (step 1111) as is the case with normal CD-SEM measurement, and then the pattern position on the wafer is calibrated by means of wafer alignment (step 1112). Next, a stage is moved to the vicinity of the measurement target pattern, and accurate positioning is achieved by using a preset pattern adjacent to the target pattern (step 1113) and the image quality is adjusted by making focus and astigmatism adjustments (step 1114). Subsequently, a measurement target pattern image is acquired (step 1115) to perform a measurement process (step 1116). FIG. 1B shows an example in which the measurement process is performed immediately after image acquisition. However, an alternative is to acquire an image and separately perform the measurement process. In such an alternative case, an image recording process (not shown) or image transfer process (not shown) should be performed instead of the measurement step (step 1116), which is shown in FIG. 1B, to record image data on a recording medium (e.g., a recording medium 301 shown in FIG. 3 or an image database 5 shown in FIG. 4). Further, an image processing unit (measurement process unit) 8, which is separately connected to an external interface 20, should perform the measurement process. If, as shown in FIG. 4 (details will be given separately), the measuring apparatus (e.g., CD-SEM 10) is connected to the image processing unit 8 via the external interface 20 such as a network, it is possible to transfer the image acquired by the CD-SEM 10 to the image processing unit 8 as required, perform the measurement process, and transfer the obtained results to a measurement result database 6. An alternative is to first transfer the image to the image database 5 and then to the image processing unit 8 and perform the measurement process. Since this alternative makes it possible to adjust the processing timing as desired, it is useful in a situation where the SEM main body can be preoccupied for a limited period of time and measurement calculations take a considerable amount of time or in a situation where no library can be prepared. When a plurality of patterns on the same wafer are to be measured, steps 1113 to 1116 are repeated as shown in FIG. 1B to perform the image acquisition and measurement processes on all the patterns. Upon completion of measurement, the wafer is unloaded (step 1117).

Figure 3:
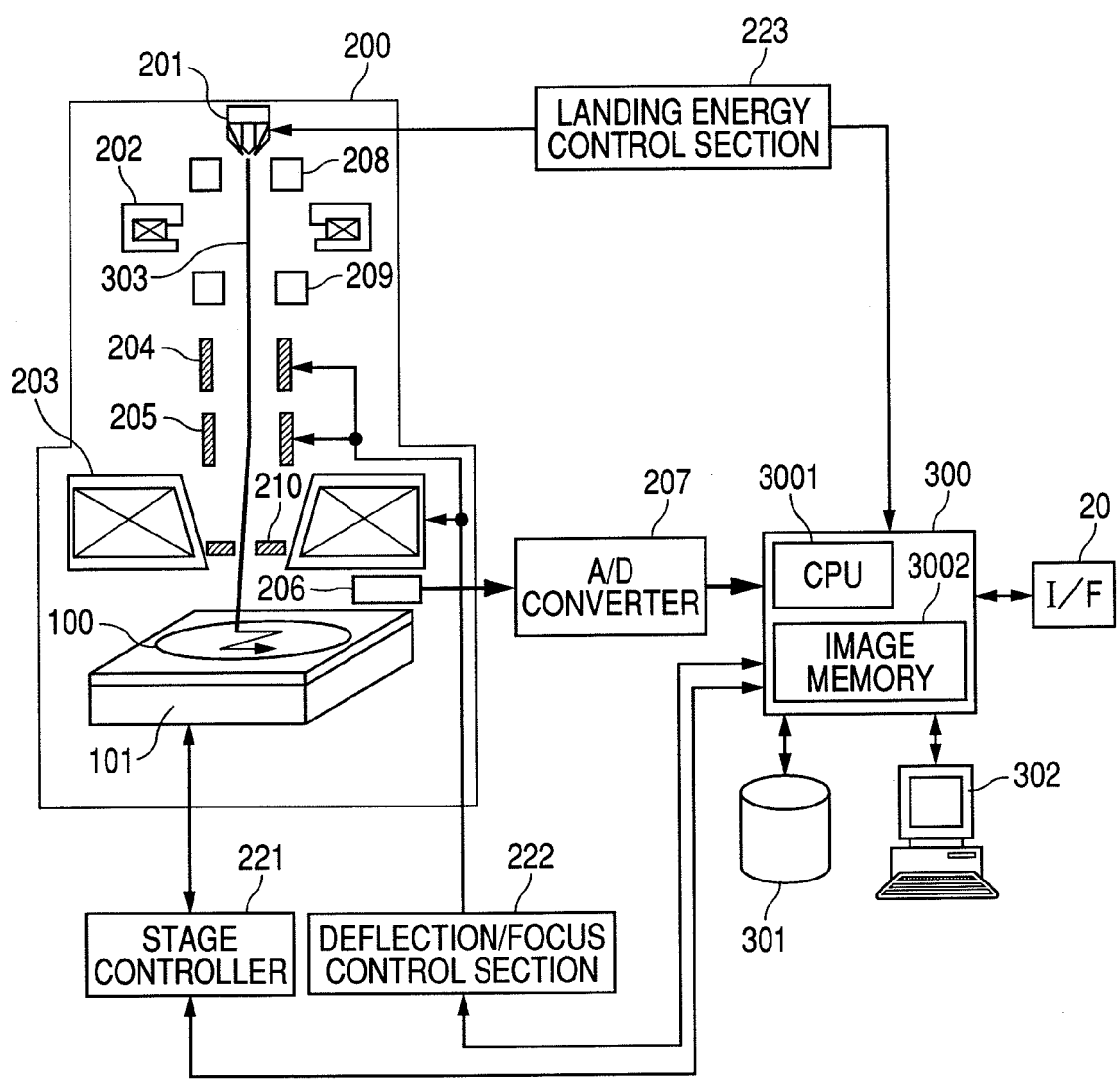
FIG. 3 is a schematic block diagram illustrating an embodiment of an SEM measurement apparatus.

An embodiment of the CD-SEM apparatus for acquiring an SEM image according to the present invention will now be described with reference to FIG. 3. In the CD-SEM apparatus 10, an electron optics 200 includes an electron gun 201, an alignment coil 208 for aligning the emission of a primary electron beam from the electron gun 201, a condenser lens 202 for converging the primary electron beam, a stigmator 209 for correcting the astigmatism in the primary electron beam, deflectors 204, 205 for subjecting the primary electron beam to two-dimensional deflection, an objective lens 203, and an objective lens aperture 210.

A specimen 100 such as a wafer is placed on an xy stage 101 and transported in xy direction by the xy stage 101. A secondary electron detector 206 detects secondary electrons, which are generated when the specimen 100 is irradiated with an electron beam, and converts the secondary electrons to an electrical signal. Consequently, a secondary electron beam image (electron beam image or SEM image) is detected.

In other words, the primary electron beam emitted from the electron gun 201 is converged by the condenser lens 202 and objective lens 203 and irradiated on the specimen 100, which is placed on the xy stage 101, as a minute spot. When the electron beam is irradiated in the above manner, the irradiated portion generates secondary electrons and backscattered electrons depending on the material and shape of the specimen. The deflectors 204, 205 perform a two-dimensional scan of the primary electron beam 303. The generated secondary electrons are then detected by the secondary electron detector 206 and converted to an electrical signal. The resulting electrical signal is further converted to a digital signal by an A/D converter 207. Consequently, a secondary electron beam image is obtained as a two-dimensional digital image. For dimensional measurements in a semiconductor process, a secondary electron beam image is generally used (instead of a backscattered electron beam image). When the term "electron beam image" or "SEM image" is hereinafter used, it denotes a secondary electron beam image. However, the present invention can be similarly applied to a backscattered electron image. It is assumed that the CD-SEM 10 has a beam tilt function and stage tilt function. A stage controller 221 controls the xy stage 101 in compliance with instructions from the processing/control section 300. A deflection/focus control section 222 controls the deflectors 204, 205 so as to set an image magnification, and controls the objective lens 203 for auto-focus control purposes in compliance with instructions from the processing/control section 300. A landing energy (accelerating voltage) control section 223 controls the landing energy in compliance with instructions from the processing/control section 300.

The obtained SEM image is then stored on the recording medium 301 and subjected to a measurement process in the processing/control section 300. Alternatively, however, the obtained SEM image may be saved in the image database 5 via the external interface 20 or directly forwarded to the image processing unit 8, and then subjected to the measurement process. The apparatus operations and the display of their results are performed through the GUI function of a display device or the like 302. The processing/control section 300 includes a CPU 3001 and an image memory 3002. The CPU 3001 is capable of incorporating a CD recipe creation function.

An embodiment of a system that includes the SEM measurement apparatus and database according to the present invention will now be described with reference to FIG. 4. The pattern measurement method according to the present invention may be exercised within the CD-SEM 10. An alternative is to let the CD-SEM merely perform an image acquisition process, transfer the obtained image to a different computer via the interface 20 such as a local area network, and process the transferred image. For example, the obtained image may be recorded in the image database 5, and subjected to calculations in the image processing unit 8 to transfer the results to the measurement result database 6. As described in conjunction with the first and second embodiments, process information and design information databases 1, 2 should be accessible for creating a recipe for width measuring image acquisition in the CD measurement recipe creation section (e.g., the CPU 3001 in the processing/control section 300) and creating, for instance, library simulation data in the simulation unit 9. Further, when the CD measurement recipe 4 is collectively managed in the form of a database, the same measurements as the pattern measurement method according to the present invention can be made with ease by a plurality of CD-SEMs 10. Since creating library data for comparison with an actual image takes a relatively long period of time, such library data is created by a computer (simulation unit 9) other than the measuring computer. Performing collective management for allowing the image processing unit 8 and CD-SEM 10 to access the SEM waveform library 3 is helpful in terms of data capacity and management. When an apparatus characteristics database 7, which is used for simulation, is on the same network, apparatus-specific characteristics can be readily reflected.

As far as an image can be created by electron beam simulation, the pattern measurement method according to the present invention produces the same effects even when an SEM other than the CD-SEM 10 is used. When, for instance, a general-purpose SEM 11 or a defect review SEM 12 is used, the use of a backscattered electron image is acceptable as far as simulation can be performed. When the data and the apparatuses using according to the present invention are interconnected via the interface 20 as described above, it is possible to achieve, easily and smoothly, the library creation reflected the characteristics of the apparatus according to the present invention and the waveform matching used the library.

In the CD-SEM, the name of the SEM measurement apparatus and image acquisition conditions are specified when measurements are made. Therefore, when the apparatus characteristics are recorded in the apparatus characteristics database 7 for each SEM measurement apparatus and each image acquisition condition set, it is possible to read the apparatus characteristics easily at the time of simulation waveform (simulated waveform) generation and reflect the read characteristics in electron beam simulation.

Next, the procedure for performing the measurement process (MBL (Model-Based Library)) will be described in detail by using FIGS. 5A and 5B.

In the CD-SEM 10, an image processing section 300 first generates waveform data 1301a or 1301b, which is to be processed, from an SEM image 1300a or 1300b, which is detected by the secondary electron detector 206, and stores the generated data on the recording medium 301 or in the image database 5. If the S/N ratio of the SEM image (waveform data) 1301a or 1301b is sufficiently good, one-line scan data should be used as it is. If the process is unstable due to an insufficient S/N ratio, data derived from several y-direction line scans should be averaged and used. In this instance, the averaging process needs to be optimized in accordance with the shape of the measurement target pattern. When a line pattern is to be measured as indicated in the upper left corner of FIG. 5A, the averaging process is performed in the direction perpendicular to the line pattern. If, in this instance, the line edge position variation (generally referred to as line edge roughness) is significant, increasing the number of average line scans averages waveforms of portions that differ in shape. Therefore, it is necessary to perform the averaging process within a range in which the influence of line edge roughness is sufficiently small. When a hole pattern is to be measured as indicated in the upper right corner of FIG. 5A, averaging should be conducted in circumferential direction. Although the subsequent explanation relates to a situation where a line pattern is to be measured, the same process can also be performed in a situation where a hole pattern is to be measured. The process described below can be applied to each line scan (or each circumferential point) in an image. Therefore, the edge position of each line scan can be accurately detected when the process is repeatedly performed while moving the target region. By the way, whether it is the line pattern or the hole pattern can be identified based on CD measurement recipe information, which is created based on the process information 1 and design information 2 and stored in the CD measurement recipe 4.

Next, the image processing section 300 or image processing unit 8 determines a processing region 1303 by detecting a peak 1302 near an edge in the actual waveform data 1301a/1301b stored on the recording medium 301 or in the image database 5. When a one-line pattern is to be measured as indicated in the upper left corner of FIG. 5A, there are only two bright peaks. Therefore, an edge in a desired evaluation direction (the right-hand edge in the figure) is selected from the two detected peaks, and a region sufficiently containing a pattern edge portion is set as the processing region. The image processing section 300 or image processing unit 8 then compares the SEM signal waveform (Img (x)) 1304 within the processing region with a prepared electron beam simulation waveform (the simulated waveform of an electron microscope signal) 1002, which is shown in FIG. 2B and stored, for instance, in the SEM waveform library 3, and selects an SEM waveform that is the most similar to the actual SEM signal waveform from the library 3, which stores SEM waveforms derived from electron beam simulations concerning various cross shapes and image acquisition conditions as indicated in FIG. 2B. The pattern shape 1003 that is the source of the most similar simulation waveform is determined as an estimated value of the actual pattern shape. As disclosed by Proc. SPIE 4689, the data in the library 3 is such that when only one edge (FIG. 2B) is subjected to electron beam simulation, the opposite edge can be similarly processed when the library 3 is reversed left to right.

Figure 5A:
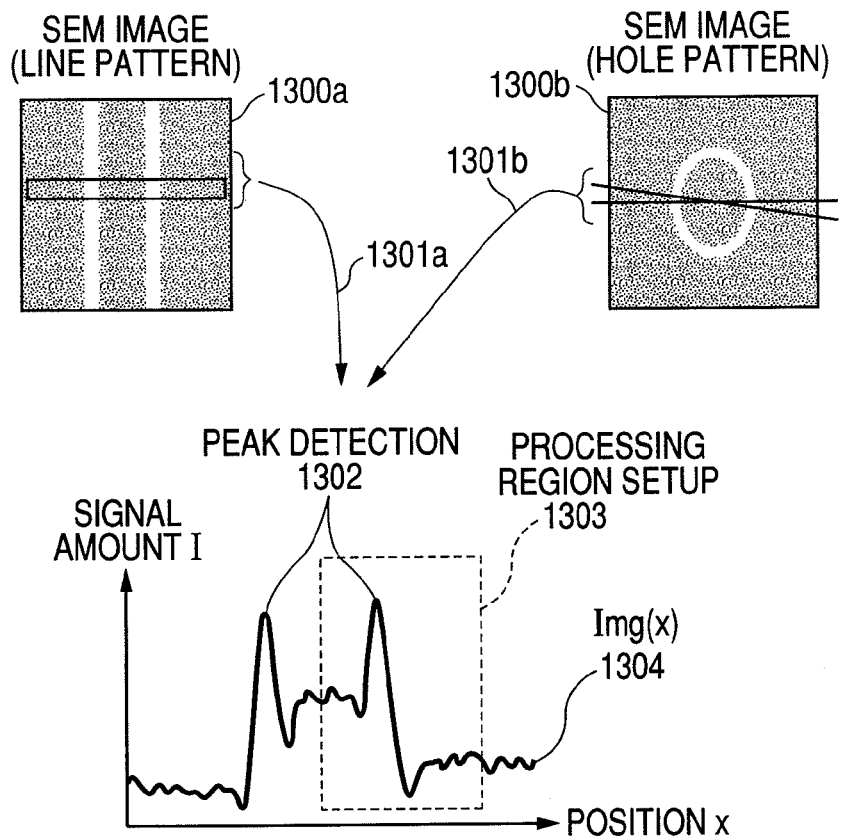
FIG. 5A shows an SEM image and a processing region for waveform data of the SEM image.
Figure 5B:
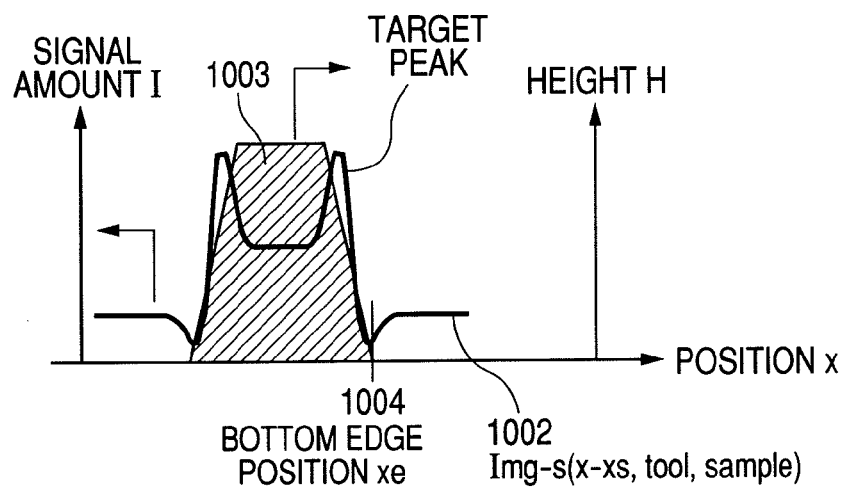
FIG. 5B illustrates the relationship between a cross-sectional pattern shape and SEM image waveform data.

FIGS. 2 and 5 illustrate a case where the dimensions of the measurement target are sufficiently great relative to the electron beam diameter and electron diffusion in a solid. However, if the pattern dimensions are small relative to the electron beam diameter and electron diffusion in a solid, the two peaks shown in FIGS. 5A and 5B may not be separated from each other. In such an instance, the above comparison process is performed using a region containing two edges without setting a region for each peak. It is necessary that the simulation unit 9 perform an electron beam simulation to generate an electron beam simulation waveform 1002 with both edges involved. An electron beam simulation should be conducted while considering the inter-edge distance and a combination of right- and left-hand sidewall angles (SWAs), which differ from each other.

The procedure for comparing the actual SEM signal waveform with an electron beam simulation waveform (the simulated waveform of an electron microscope signal), which is performed by the processing/control section 300 or image processing unit 8, will now be described. When, as shown in FIGS. 5A ad 5B, the actual SEM signal waveform 1304 is Img(x) and the electron beam simulation waveform is Img-s (x-xs, tool, sample), the error E between the two signal waveforms can be expressed by Equation (1).

$$E = \Sigma \{\text{Img-}s(x\text{-}xs, \text{tool}, \text{sample}) - \text{Img}(x)\}^2 \qquad \text{Equation (1)}$$

where, the symbol "Σ" is the sum of signals at position x of all pixels within the processing region 1303; the symbol "xs" is a shift amount of the electron beam simulation waveform; the symbol "tool" is a set of CD-SEM apparatus parameters (apparatus characteristics) including the parameters for image acquisition conditions (electron beam landing energy, beam shape, image acquisition magnification (pixel size), etc.); and the symbol "sample" is a set of target shape parameters that are shown, for instance, in FIG. 2A. The symbol "sample" includes, for instance, H (height), SWA (sidewall angle), and BW (bottom width) shown in FIGS. 2A and 2B. The symbol "tool" will be described in detail later. When a combination of "xs," "tool," and "sample" for minimizing the error E is determined by a nonlinear least-squares method such as the Levenber-Marquardt method, it is possible to estimate three-dimensional shape information (H, SWA, BW, TR, BR, etc.) and correct pattern edge position information. When, for instance, a bottom edge position (xe) 1004 in FIG. 5B and a matching result (xs) are used, the sample edge position of the actual waveform (FIG. 5A) is expressed by xe+xs. When the right- and left-hand edge positions are determined in this manner, a correct CD value can be determined from the difference between the right- and left-hand edge positions.

The first embodiment predetermines the CD-SEM apparatus parameters, which are among the above-mentioned parameters, from the design values (30 in FIG. 8) of the above apparatus, which are entered, for instance, by input means (including a GUI) 302, 13, for instance, in the simulation unit 9, and registers the predetermined parameters, for instance, in the apparatus characteristics database 7. The input means is not limited to the input means 302 shown in FIG. 3 or the input means 13 shown in FIG. 4. Alternatively, the above-mentioned design values may be entered from an apparatus design system (not shown) via the network 20. Another alternative would be to perform setup by entering apparatus parameters (electron optics resolution, beam divergence half angle, aberration coefficients, etc.) for imaging electron optics conditions for the SEM used for measurement, for instance, in the simulation unit 9 in accordance with values determined in an apparatus design phase.

Figure 6A:
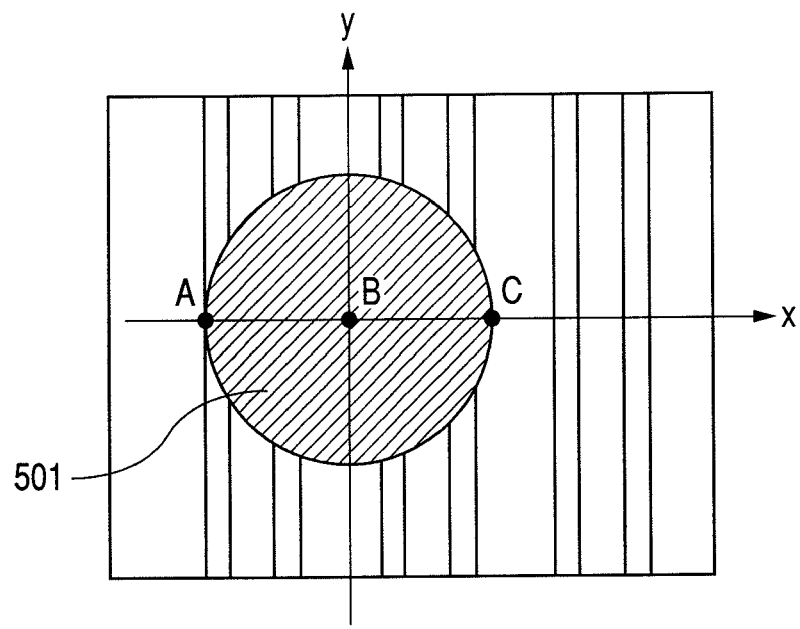
FIG. 6A is a combination of a top view of a semiconductor pattern and a cross-sectional view of an electron beam.
Figure 6B:
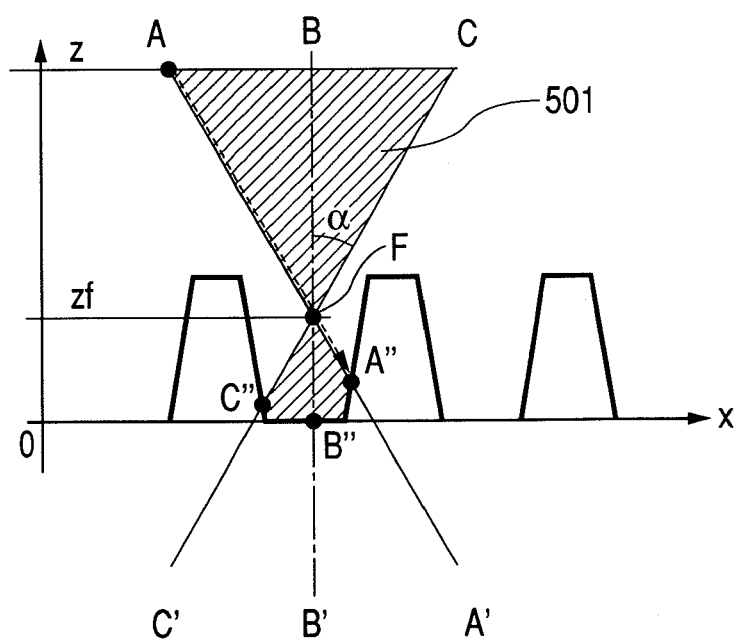
FIG. 6B is a combination of a lateral cross-sectional view of a semiconductor pattern and a cross-sectional view of an electron beam.
Figure 6C:
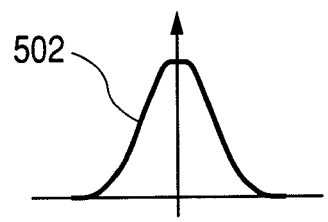
FIG. 6C shows an electron beam intensity distribution.

An embodiment of the method for allowing, for instance, the simulation unit 9 to reflect the electron optics conditions, which are the apparatus characteristics (electron optics resolution, beam divergence half angle, aberration coefficients, etc.), in an electron beam simulation will now be described with reference to FIGS. 6A to 6C. FIGS. 6A to 6C illustrate an electron beam that is irradiated on a semiconductor pattern. FIG. 6A is a top view (a view from the beam irradiation direction). FIG. 6B is a side view (a view from the longitudinal direction of a line pattern shown in FIG. 6A). The shaded portions represent an electron beam 501. In other words, the figures illustrate a simplified model that represents an electron passage range. As shown in FIG. 3, the objective lens 203 causes the electron beam 303 to converge on the surface of the specimen 100. In an example that is shown in FIGS. 6A to 6C, all electrons passing through the objective lens converge toward point F, which is positioned at a focusing height zf, and then diffuse again. More specifically, electrons emitted from points A, B, and C pass through point F and travel toward points A', B', and C'. In reality, however, the electrons enter a solid through the specimen surface (e.g., point A"), and diffuse to generate secondary electrons. The illustrated angle α is a beam divergence half angle. It is substantially determined according to the design and use conditions for the electron optics 200. As disclosed by Proc. SPIE 5752, the beam divergence half angle works to distort the effective beam shape prevailing at a pattern edge. Therefore, if an electron beam simulation is performed without considering the beam divergence half angle, a significant measurement error occurs. The beam divergence half angle can be calculated when, for instance, the simulation unit 9 makes an electromagnetic field analysis in accordance with the input design information about the electron optics 200. In FIG. 6B, the beam width at point F is zero. In reality, however, it is not perfectly zero due to various aberrations and inter-electron Coulomb repulsion. Further, since sampling is conducted with pixels having a finite size, the resolution of the resulting image also varies with the pixel size. Thus, the convolution of a predefined electron intensity distribution 502 (e.g., two-dimensional Gaussian distribution) shown in FIG. 6C with an electron trajectory shown in FIGS. 6A to 6C is used as a model that expresses the beam irradiation state and the influence of pixel size. The same result is obtained no matter whether the convolution of intensity distribution is performed in relation to a simulation electron trajectory or a waveform derived from simulation. This model is the same as the model disclosed by Proc. SPIE 5038 (FIG. 2). However, the present invention sets the beam divergence half angle α in accordance with the design values of the electron optics 200.

Further, the simulation unit 9, for example, performs a Monte Carlo simulation so that all electrons fall on the specimen surface through point F, and calculates the amount of secondary electron emission at each beam position while assuming that the beam intensity distribution is uniform in a plane perpendicular to the optical axis (in a plane that is parallel to the plane containing points A, B, and C) within a circular cone that is shaded in FIGS. 6A and 6B. The electron beam simulation according to the Monte Carlo method is described in detail, for instance, by J. R. Lowney, "Monte Carlo Simulation of Scanning Electron Microscope Signals for Lithographic Metrology," SCANNING Vol. 18, pp. 301-396 (1996) and by D. C. Joy, Monte Carlo Modeling for Electron Microscopy and Microanalysis, OXFORD UNIV. PRESS (1995).

Although details are not given here, the simulation unit 9, for example, sets the shape and material of a measurement target sample that is obtained from the CD measurement recipe database 4 and shown in FIGS. 2A and 2B. Next, the simulation unit 9 can assume an intensity distribution within the shaded circle in FIG. 6A in accordance with the intensity distribution of electrons emitted from an electron source and randomly give coordinates within the circle by using random numbers conforming to the intensity distribution. The trajectory of electrons passing the focus point F is determined with the given coordinates representing a start point, and a physical-model-based calculation is performed to determine the scatter trajectory of incident electrons in the solid and the generation of secondary electrons in accordance with the energy of the electrons and the position and direction of electron incidence on the specimen surface. This calculation is repeatedly performed on electrons that are incident from various start points and at various angles, which are determined by various random numbers. The obtained results are added together to simulate the generation of secondary electrons arising from the specimen surface and calculate the signal amount. The scattering in the solid is a probabilistic phenomenon, and it is known that the use of a random-number-based Monte Carlo simulation is effective. The library creation step (step 1200) according to the present invention sets the spread of electrons and the variations in the direction of incidence in a case where a beam irradiates on a certain point in accordance, for instance, with the above-mentioned beam irradiation model, and uses the number of secondary electrons detected upon the incidence of the electrons as the SEM image signal amount. When the image brightness prevailing at each point is detected while the beam irradiation target position is sequentially changed, it is possible to acquire an SEM image simulation signal.

The focus position zf varies depending on how an electron beam is focused. In FIGS. 6A to 6C, zf=0 when the surface of a sample substrate is in focus. The value zf should normally be set to a predetermined height such as the height of the specimen surface. The simulation in the first embodiment is performed while assuming that the value zf is equal to zero or other fixed value. A standard zf value can be obtained by variously changing the value zf, performing simulations with the various zf values, operating the actual apparatus to perform an AF (auto-focus) image process on an image obtained from the SEM apparatus, and selecting the zf value that provides the best focus in the actual apparatus.

Figure 7A:
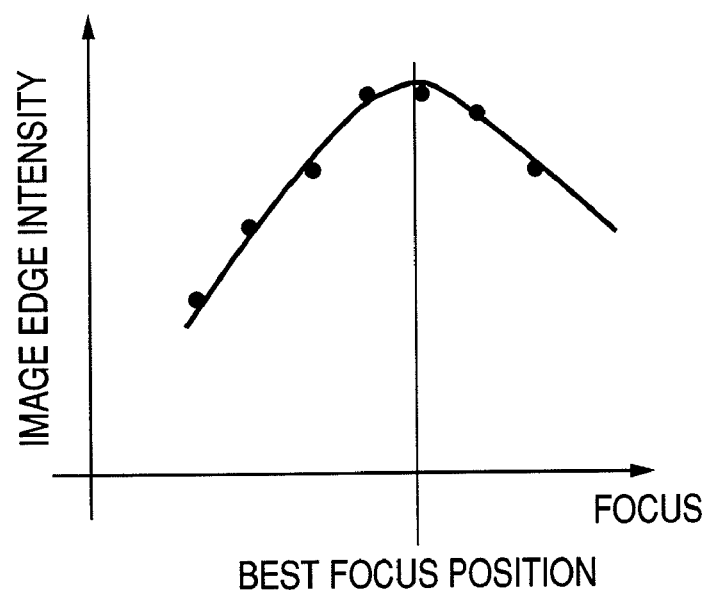
FIG. 7A is a graph illustrating the relationship between an electron beam focus position and image edge intensity.
Figure 7B:
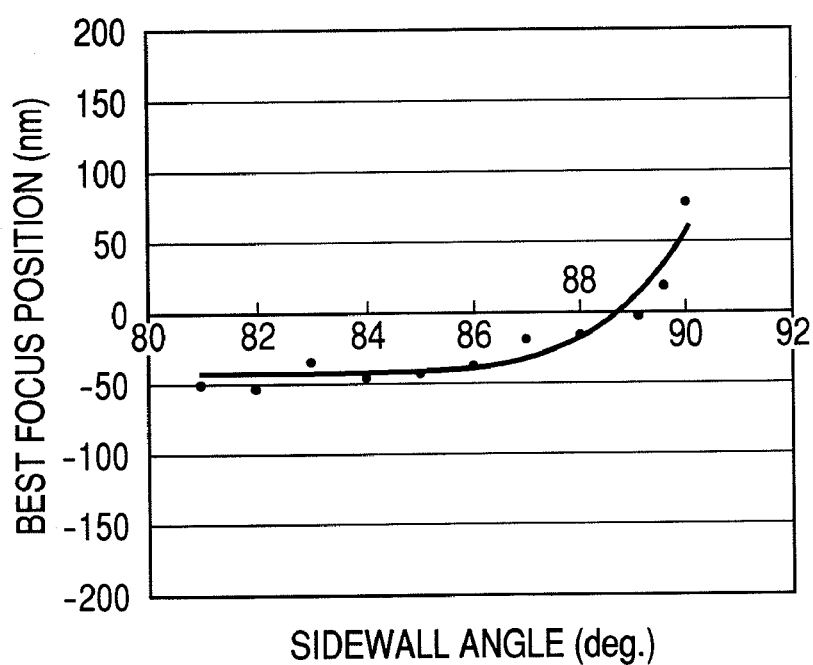
FIG. 7B is a graph illustrating the relationship between a pattern sidewall angle and best focus position.

FIGS. 7A and 7B illustrate an example in which electron beam simulations are performed on various sample sidewall angles (SWAs) while the focus is varied. First of all, the image edge intensity is calculated in relation to images that are obtained with the focus of each sidewall angle varied as shown in FIG. 7A. The term "edge intensity" refers to a value that indicates the intensity of an edge in an image. The same evaluation method as for automatic focusing in the actual SEM apparatus should be used here. For example, a Sobel filter output may be used. Next, the focus position at which the edge intensity is maximized is calculated from changes in the edge intensity as the best focus position. Peak detection can be accomplished with ease when, for instance, the data shown in FIG. 7A is subjected to quadratic curve fitting.

FIG. 7B shows an example in which the best focus position is determined for various pattern shapes. In the example shown in FIG. 7B, the best focus position varies with the sidewall angle of a target sample. FIG. 7B shows sidewall angle changes only. In reality, however, the same process is performed on various shapes in the library 3. As described above, the conditions for allowing the SEM apparatus to acquire an SEM image representing the best focus in accordance with the measurement target shape can be reproduced by performing an electron beam simulation.

If the auto-focus system is sufficiently stable, the use of the library 3 that stores only simulation images obtained at the best focus position (zf for each set of conditions) eliminates the necessity for estimating the beam shape, focus position, and other parameters. In a situation where the relationship between the cross section shape and best focus position is obtained as indicated in FIG. 7B and an appropriate function can be applied to such relationship, storing the function may make it easy to perform a library creation or other process (a quartic function is used in the example shown in FIG. 7B). In this case, high-speed, consistent (stable) measurements can be made because beam shape estimation is not performed.

If the AF (auto-focus) process of the SEM apparatus is not sufficiently stable, the simulation unit 9, for example, performs a simulation on some zf values within an AF variation range and records (stores) the resulting waveforms in the library 3. Selecting a waveform that is the most similar to the actual waveform upon each measurement within the recorded zf range in the same manner as for the other apparatus parameters makes it possible to make high-precision measurements while considering beam shape changes. The AF characteristic of the actual apparatus can be easily measured when the same location is subjected to auto-focusing a number of times to measure the degree of the resulting change in the control value of the objective lens 203. When the minimum beam shape variation range is set in accordance with AF performance, high-speed, consistent (stable) measurements can be made.

Figure 8:
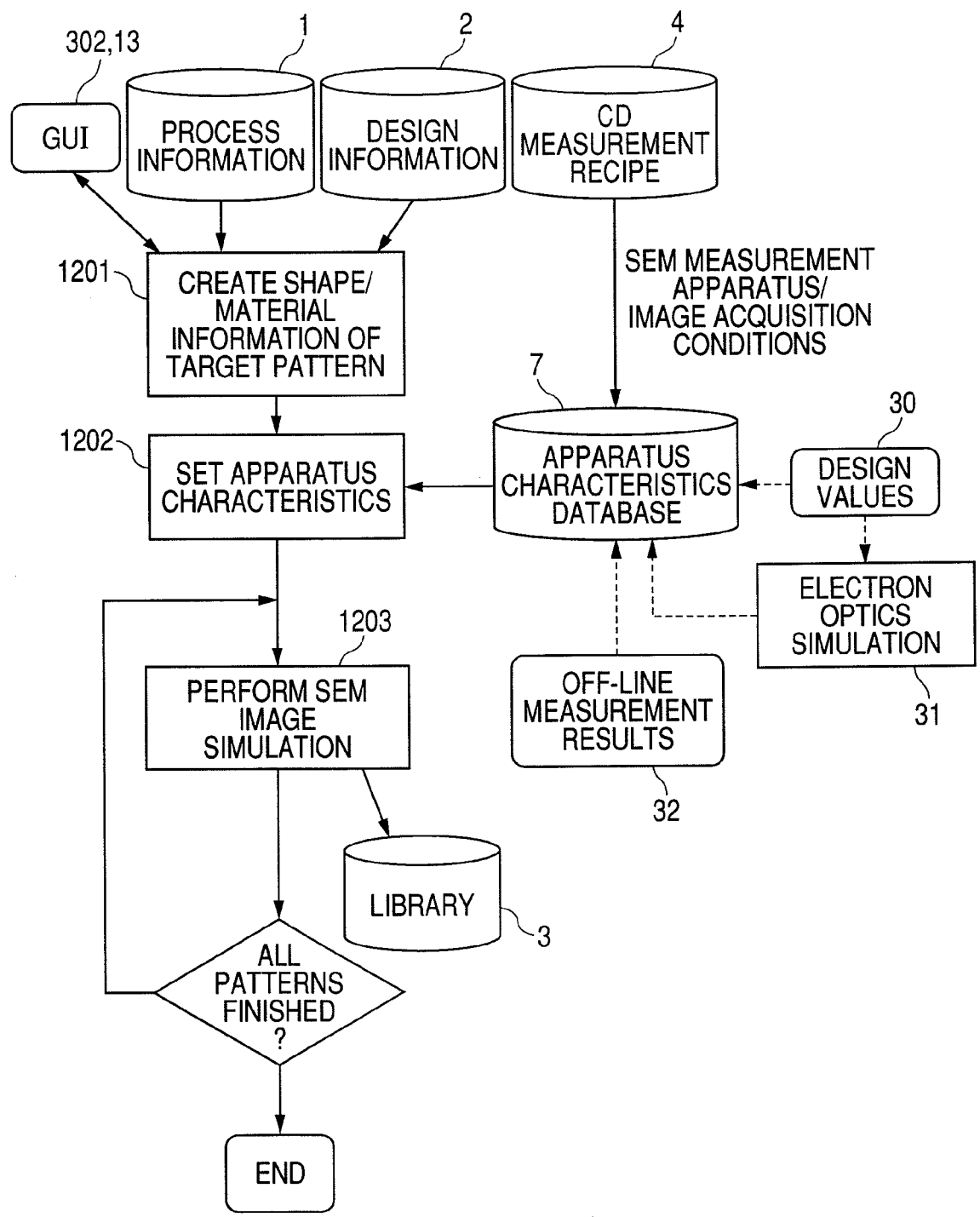
FIG. 8 illustrates an embodiment of a procedure for creating simulation library for pattern measurement.

As described above, the simulation unit 9, for example, performs a simulation into which a model based on the beam divergence half angle and focus position is introduced while using, for instance, a two-dimensional Gaussian filter 502 as indicated in FIG. 6C to adjust for the actual waveform. The adjustment should be made by changing the size of the Gaussian filter as described in Proc. SPIE 4689, making comparison with the actual waveform, and selecting a waveform that is the most similar to the actual waveform. If a sample having a known three-dimensional shape is available in this instance, it is possible to accomplish estimation while only the apparatus parameters are stabilized. Therefore, a calibration sample is handy. Under normal conditions, the filter size should be set once for a set of beam irradiation conditions (landing energy, pixel size (image magnification), etc.). The beam divergence half angle, focus position, Gaussian filter size, and the like are recorded (stored) in the apparatus characteristics database 7, which is shown in FIG. 8 and will be described later. Although the Gaussian filter is used here to compensate for the difference in the beam shape, different density distribution functions may be used for tool-to-tool matching.

For example, the processing/control section 300 or image processing unit 8 notes various combinations of target shape parameters (sample) other than the apparatus parameters (tool) and the shift amount (xs), and uses a nonlinear least-squares method (e.g., Levenber-Marquardt method) to determine the combination that minimizes the error E in Equation (1). Consequently, the resulting shift amount (xs) and target shape parameters (sample) represent the measurement target shape and the positions of their edges, which are estimated from the acquired measurement target SEM image and simulation library 3.

The data corresponding to the target shape parameters exist only under conditions where an electron beam simulation is performed. Therefore, only discrete values can be selected when a selection is made from the library 3. However, when, for example, the simulation unit 9 interpolates the data as described in Proc. SPIE 4689, simulation signal waveforms can be calculated for intermediate values that do not exist in the library 3. When, for instance, a simulation signal for a sidewall angle of 3.2 degrees is to be obtained in a situation where the library 3 contains data about sidewall angles of 3 and 4 degrees, Equation (2) below should be used:

$$\text{Img-}s(x, 3.2 \text{ deg.}) = \text{Img-}s(x, 3 \text{ deg.}) + (\text{Img-}s(x, 4 \text{ deg.}) - \text{Img-}s(x, 3 \text{ deg.})) \times (3.2-3)/(4-3) \quad \text{Equation (2)}$$

Proc. SPIE 4689 performs a simulation with only a beam parallel to the z-axis without considering the beam divergence half angle α as indicated in FIGS. 6A to 6C, performs gradation conversion in accordance with gain and offset in relation to the resulting simulation waveform, and performs convolution with the Gaussian filter in order to simulate a finite beam shape. The shift amount and target shape parameters are simultaneously estimated by using the gain, offset, and Gaussian filter size as the SEM apparatus parameters in accordance with a nonlinear least-squares method based on the error in Equation (1).

Meanwhile, the present invention predetermines some or all of the SEM apparatus parameters (the apparatus characteristics of the electron microscope) in accordance with the design values of the electron optics or the values measured by the measurement means, and does not use them as the estimation parameters for the nonlinear least-squares method. In this manner, the number of parameters to be estimated can be reduced. When the nonlinear least-squares method is used, the time required for estimation increases with an increase in the number of parameters to be estimated. If similar signal waveforms are given with a certain number of parameter combinations, the results might not converge. If there are a large number of parameters, the estimation accuracy for each parameter may decrease due to the influence of noise, thereby reducing measurement repeatability. Meanwhile, the present invention predetermines the SEM apparatus parameters by a different method. Therefore, the present invention can avoid vagueness in parameter estimation and make consistent, high-speed measurements. When a simulation is performed with a model that is more accurate than a model used with a conventional method, the number of parameters generally increases as indicated in FIGS. 6A to 6C, thereby increasing the time required for calculations and resulting in a failure to obtain correct results. However, the present invention fixes or restricts the parameters in accordance with the apparatus characteristics. This prevents the amount of calculations from increasing and makes it possible to use a more accurate model. Although the present embodiment assumes the use of a secondary electron image, a waveform library can also be created by performing a simulation through the use of backscattered electrons or transmitted electrons. The same advantages can be provided by applying the method according to the present invention.

Second Embodiment (Reflecting the Information Obtained at a Design Phase-1: Registering Characteristics on an Individual Condition Set Basis)

(Reflecting the Information Obtained at a Design Phase-2: Registering Characteristics on an Individual Electron Optics Simulation/Condition Set Basis)

A second embodiment will now be described with reference to a specific procedure for reflecting the apparatus characteristics in an SEM image simulation. The second embodiment relates to the details of step 1200, which is shown in FIG. 1A. As described in conjunction with the first embodiment, the apparatus characteristics of the CD-SEM can be set from the design values if the information about incorporated performance characteristics is available. For example, the electron beam shape and aberration coefficients can be calculated by performing an electromagnetic field analysis in accordance with the design information about the electron optics. The electromagnetic field analysis is made to calculate the electric field and magnetic field for elements of the electron optics 200 from, for instance, the dimensions and arrangement of the elements and the voltages applied to them, and determine the trajectory of electrons in the electromagnetic field. The electromagnetic field analysis is performed according, for instance, to the finite difference method or finite element method.

FIG. 8 illustrates the details of a simulation library creation procedure that reflects the apparatus characteristics and is to be performed, for instance, by the simulation unit 9. First of all, the simulation unit 9, for example, creates a list of shape and material information of target pattern for creating the library 3 (step 1201). In this instance, an objective shape of the pattern to be formed by the manufacturing process should be set as the basic shape of a target sample. Further, a simulation for library creation should be performed while considering the measurement range (predicted shape variation range), which indicates the desired degree of shape variation from the objective shape. The objective shape can be set with relative ease when design information 2 such as design data etc. is used. For an electron beam simulation according to the Monte Carlo method, the material information about each structure is needed. Such information can be set with the process information 1. It goes without saying that the operator may use the input means 302 or the like to enter the information about the shape and material.

Figure 9A:
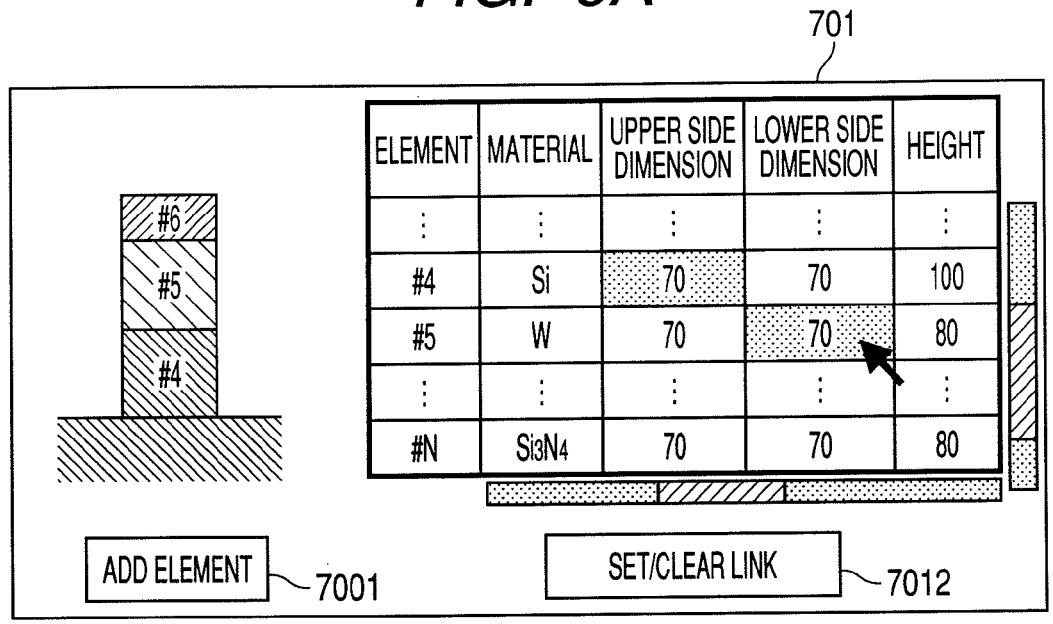
FIG. 9A shows an embodiment of a GUI for creating line pattern data by combining trapezoidal shapes.
Figure 9B:
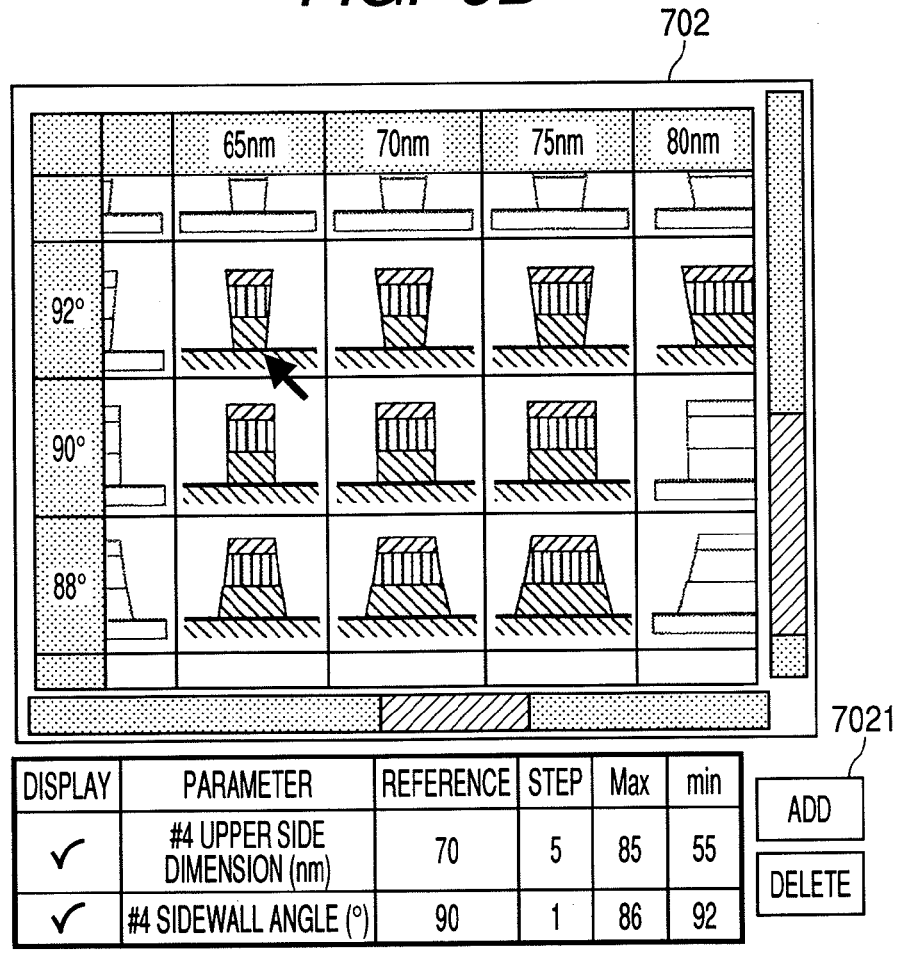
FIG. 9B shows an embodiment of a GUI and illustrates a case where the width and sidewall angle of element #4 are to be changed.

FIGS. 9A and 9B illustrate an example of a graphical user interface (hereinafter referred to as the GUI) that is used, for instance, with the display device 302 shown in FIG. 3 as an aid for entering a measurement target shape with reference to the objective shape. Although FIGS. 9A and 9B illustrate an example of line pattern data creation based on the combinations of trapezoidal shapes, this example can also be applied to the other shapes. First of all, the reference shape is created with the GUI 701 shown in FIG. 9A. Data is added as needed to match the number of trapezoids to be superposed on an under layer (or a plurality of under layers although the figure shows only one layer).

In the example shown in the figure, the number of trapezoidal elements can be increased by pressing the "Add Element" button 7011. Therefore, it is possible to stack an appropriate number of trapezoids. When the material and representative dimensions of each trapezoidal element are entered in the table on the right-hand side, the displayed left-hand drawing changes accordingly. This reference data input operation may be automated to some extent by using the design information 2 and process information 1. Further, link setup may be performed so that neighboring sides, such as the upper side of trapezoidal element #4 and the lower side of trapezoidal element #5, are of the same dimension at all times. For example, selecting one dimension from the table, pressing the "Set/Clear Link" button 7012, and selecting the other dimension should set up a link. If link setup is performed so that changing one dimension automatically changes the linked dimension until it equals to the former dimension, it is easy to create the data about a complicated laminated structure. The color of linked table cells should be changed as indicated in FIG. 9A to indicate that a link is set up.

After the reference shape and dimensions are determined by using the GUI 701 shown in FIG. 9A, shape variations for library creation are set up. FIG. 9B shows an example in which the width and sidewall angle of element #4 are to be changed with a GUI 702. The "Add" button 7021 is pressed to select the parameter to be changed in relation to the reference dimensions that are set up in FIG. 9A. The change step, maximum value, and minimum value are set for the selected parameter as shown in FIG. 9B. When the "Display" column at the leftmost end is checked, simulation candidates are displayed together with the selected parameter as indicated in the upper table in FIG. 9B. When unnecessary items are selected and removed while viewing the table, setup can be easily performed so that only a necessary library can be created while viewing the target shape. In FIG. 9B, for example, the selected items are hatched whereas unselected items are indicated by lines only. As described above, the information about shape and material of the target pattern is created by using the GUIs 701, 702 (step 1201 in FIG. 8).

Next, the simulation unit 9, for example, sets the CD-SEM apparatus characteristics to be reflected in an SEM image simulation (step 1202 in FIG. 8). Each apparatus is usually assigned an ID number for management. Therefore, the ID number for managing the apparatus stored in the CD measurement recipe database 4 and the image acquisition conditions (electron beam landing energy, beam shape, image acquisition magnification (pixel size), etc.) recorded in the CD measurement recipe created in step 1101 in FIG. 1 are used to read the CD-SEM apparatus characteristics parameters for the apparatus and conditions for image acquisition from the apparatus characteristics database 7. The results are then set as the apparatus characteristics. The apparatus characteristics recorded in the apparatus characteristics parameter database are the electron optics resolution and other design values, the electron beam intensity distribution calculated by performing an electromagnetic field analysis based on electrode arrangement and other lower-order design information, or the results of off-line measurements of apparatus characteristics.

The simulation unit 9, for example, performs an SEM image simulation (step 1203) by using the shape information and the material information of the target pattern set in step 1201 and the apparatus characteristics set in step 1202, and records the results in the library 3. For one reference shape, calculations are performed on all the shape variations that are set with the GUIs 701, 702 shown in FIGS. 9A and 9B.

As described above, the library 3 is created for a combination of the sample ("sample") and apparatus ("tool"). As regards a library of general shapes such as photoresist line patterns and silicon line patterns, a library containing all conceivable shapes may be created. Further, the shapes within the shape variation range required for the process targeted for measurement may be selected to create a library for the sample. This case has the advantage that when the library 3 is created first, library creation can be quickly achieved at the time of measuring a new process.

As described above, the present invention predetermines some or all of the apparatus parameters in accordance with the design values or measured values, and creates the library 3 by performing an electron beam simulation reflected the predetermined apparatus parameters. The apparatus parameters need not be estimated by the nonlinear least-squares method; therefore, the number of parameters to be estimated can be reduced. When the nonlinear least-squares method is used, the time required for estimation increases with an increase in the number of parameters to be estimated. If similar signal waveforms are given with a certain number of parameter combinations, the results might not converge. If there are a large number of parameters, the estimation accuracy for each parameter may decrease due to the influence of noise, thereby reducing measurement repeatability.

Meanwhile, the present invention predetermines the apparatus parameters by a different method. Therefore, the present invention can avoid vagueness in parameter estimation and make stable, high-speed measurements. Although the present embodiment assumes the use of a secondary electron image, a waveform library can also be created by performing a simulation through the use of backscattered electrons or transmitted electrons. The same advantages can be provided by applying the method according to the present invention.

Third Embodiment (Reflecting the Actual Apparatus Status-1: Resolution Measurement)

A third embodiment of the procedure for creating the apparatus characteristics database 7 in step 1202, which is shown in FIG. 8, will now be described. As the third embodiment, the procedure for evaluating the CD-SEM resolution with an actual image and reflecting the evaluation result in the library or matching will be described with reference to FIGS. 10A and 10B. It is difficult to obtain exactly the same performance from apparatuses manufactured in the same manner because, in reality, the employed parts vary from one unit to another and the accuracy in assembly and adjustment is limited. Even when the same CD-SEM model is manufactured, the resolution slightly varies from one unit to another. As a result, when the same sample is measured, the measured values vary from one unit to another. The third embodiment of the present invention measures the characteristics of each tool in advance, reflects the measurement results in the library, and performs the same process as in the first embodiment to make high-precision measurements that do not vary from one unit to another.

Figure 10A:
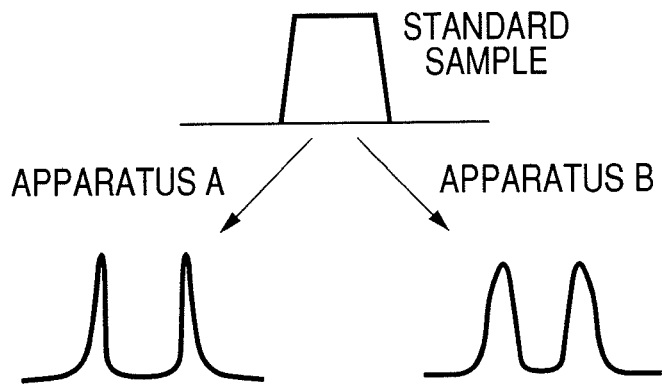
FIG. 10A shows examples of SEM image waveform data that are obtained when a standard sample is imaged by SEM measurement apparatus A and SEM measurement apparatus B.
Figure 10B:
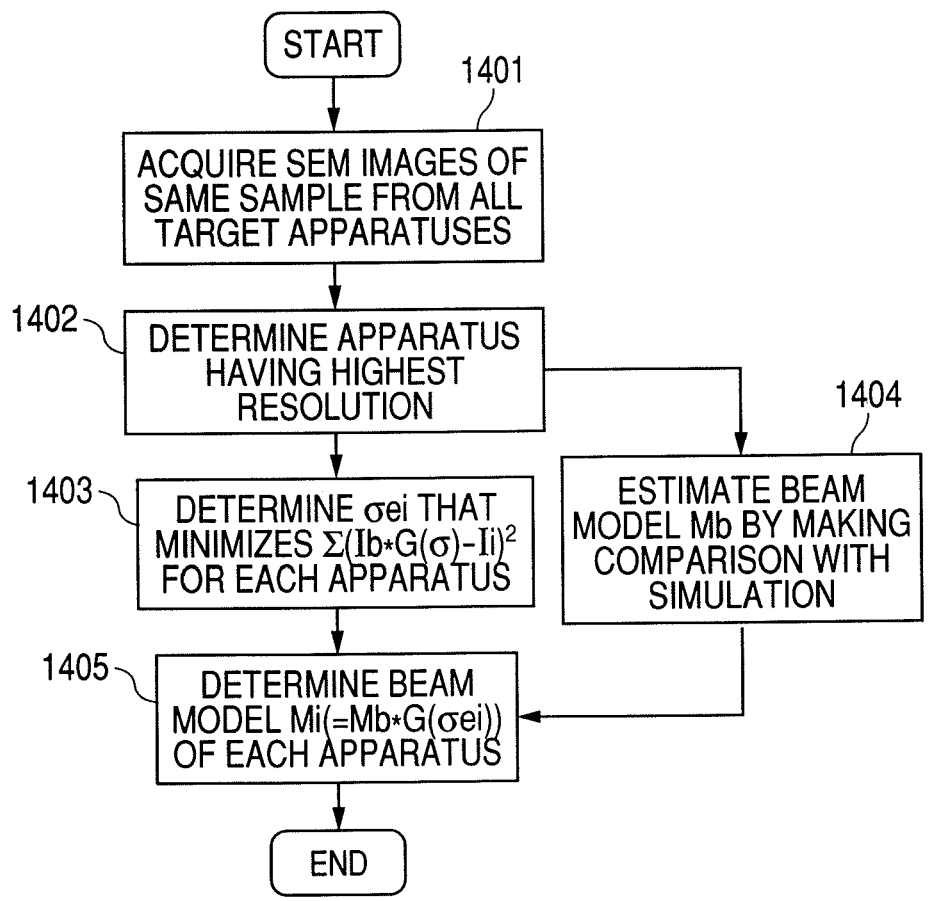
FIG. 10B is a flowchart illustrating a procedure for compensating for the electron beam resolution difference between a plurality of SEM measurement apparatuses.

As regards the third embodiment, the procedure for acquiring images of a plurality of apparatuses by using a reference sample and determining the beam characteristics parameters will be described with reference to FIGS. 10A and 10B. When the SEM image of the reference sample (the same sample or samples having the same shape and different in the material) is picked up at a plurality of apparatuses, different waveforms are detected depending on the resolutions of the apparatuses as shown in FIG. 10A. In the case shown in FIG. 10A, apparatus A has a higher resolution than apparatus B. Measurements that do not vary from one unit to another can be achieved by performing the above image acquisition process on all target apparatuses and correcting library data or measured images. FIG. 10B shows the procedure. First of all, the SEM images of the reference sample are acquired from all apparatuses (n units) as tool-tool-disparity evaluation SEM images (step 1401). Next, the images of the apparatuses are evaluated to determine the apparatus having the highest resolution (step 1402). Various methods for evaluating the resolution with an actual image have been proposed. Therefore, one of such existing methods may be used. The method disclosed, for instance, by Japanese Patent JP-A No. 142021/2003 (CG method) evaluates the resolution by using the density (brightness) gradient of each local region within an image. Further, an evaluation method based, for instance, on FFT, autocorrelation, and crosscorrelation is described by D. C. Joy, Y. Ko, and J. Hwu, "Metrics of resolution and performance for CD-SEMs," Proc. SPIE 3998, pp. 108-114 (2000) (hereinafter referred to as Proc. SPIE 3998).

Subsequently, the simulation unit 9, for example, compares the waveform obtained by applying the Gaussian having a standard deviation of $\sigma i$ to the image Ib of the apparatus having the highest resolution with the waveforms Ii of the apparatuses (the symbol i corresponds to an apparatus; e.g., i=1, 2, ... n, i≠b), and determines the value $\sigma i = \sigma e i$ that minimizes the error Eb obtained for the waveform of each apparatus from Equation (3).

$$Eb = \Sigma (Ib \times G(\sigma i) - Ii)^2 \qquad \text{Equation (3)}$$

Meanwhile, for the apparatus having the highest resolution, the simulation unit 9, for example, makes comparison with a beam model that is set according to the design values 30, as is the case with the first embodiment, and determines a beam irradiation model Mb (e.g., a beam irradiation having a divergence half angle of $\alpha$ and a Gaussian convolution in which a $\sigma = \sigma b$) that incorporates the difference from the simulation (step 1404). If the correct shape of the reference sample is known at the time of determining the beam characteristics model Mb of the apparatus having the highest resolution, the beam shape model can be constructed with relative ease from the difference between the actual waveform and the result of an electron beam simulation performed on the known shape. When steps 1401 to 1404 are completed, it is possible to determine the beam characteristics model Mb of the apparatus having the highest resolution and the filter size $\sigma i$ for adjusting the difference between the beam characteristics model Mb and the apparatuses. In other words, it is possible to determine the beam irradiation model Mi=Mb×G(σei) of each apparatus (step 1405). Consequently, the beam irradiation model Mi of each apparatus, which is based on the off-line measurements 32 of the apparatus characteristics, is recorded (stored) in the apparatus characteristics database 7 as indicated in FIG. 8.

The procedure for using the above results to make measurements that do not vary from one unit (machine) to another will now be described. When the library 3 that is filtered by a Gaussian filter of the previously detected size is created for each apparatus at the time of creating the library in accordance with the first embodiment, the processing/control section 300 or image processing unit 8 can make measurements in consideration of difference between tools. A new library may be created as the library for the apparatuses by filtering all waveforms by a Gaussian filter. An alternative is to use a Gaussian filter at the time of matching. The former decreases the calculation time but increases the capacity (size) of the library. The latter allows the apparatuses to share the same library but slightly increases the calculation cost.

Another alternative is to create the library 3 in accordance with the apparatus having the lowest resolution, filter each image in accordance with a lowest-resolution image, and make measurements by using the filtering results.

Although the Gaussian filter is used here to compensate for the difference in the beam shape, different density distribution functions may be used depending on the cause of too-tool-disparity. The apparatus characteristics evaluations should be measured once and registered if the apparatus is stable. If the apparatus is not stable, the apparatus characteristics evaluations should be measured and registered again depending on the frequency of variation. For example, the apparatus characteristics evaluations should normally be measured once a week and should be measured when an electron gun chip or other SEM part is replaced.

As described above, the method according to the present invention uses, for instance, the simulation unit 9 to create the library 3 by performing an electron beam simulation in which previously measured apparatus characteristics are reflected. Since the difference in the apparatus characteristics is reflected beforehand in the library in the above manner, it is possible to reduce the measurement error that may be caused by inter-apparatus difference and changes with time. The apparatus parameters need not be estimated by the nonlinear least-squares method; therefore, the number of parameters to be estimated can be reduced. When the nonlinear least-squares method is used, the time required for estimation increases with an increase in the number of parameters to be estimated. If similar signal waveforms are given with a certain number of parameter combinations, the results might not converge. If there are a large number of parameters, the estimation accuracy for each parameter may decrease due to the influence of noise, thereby reducing measurement repeatability. Meanwhile, the present invention predetermines the apparatus parameters by a different method. Therefore, the present invention can avoid vagueness in parameter estimation and make consistent (stable), high-speed measurements of a plurality of apparatuses for a long period of time.

Fourth Embodiment (Reflecting a Spherical Aberration)

Figure 11:
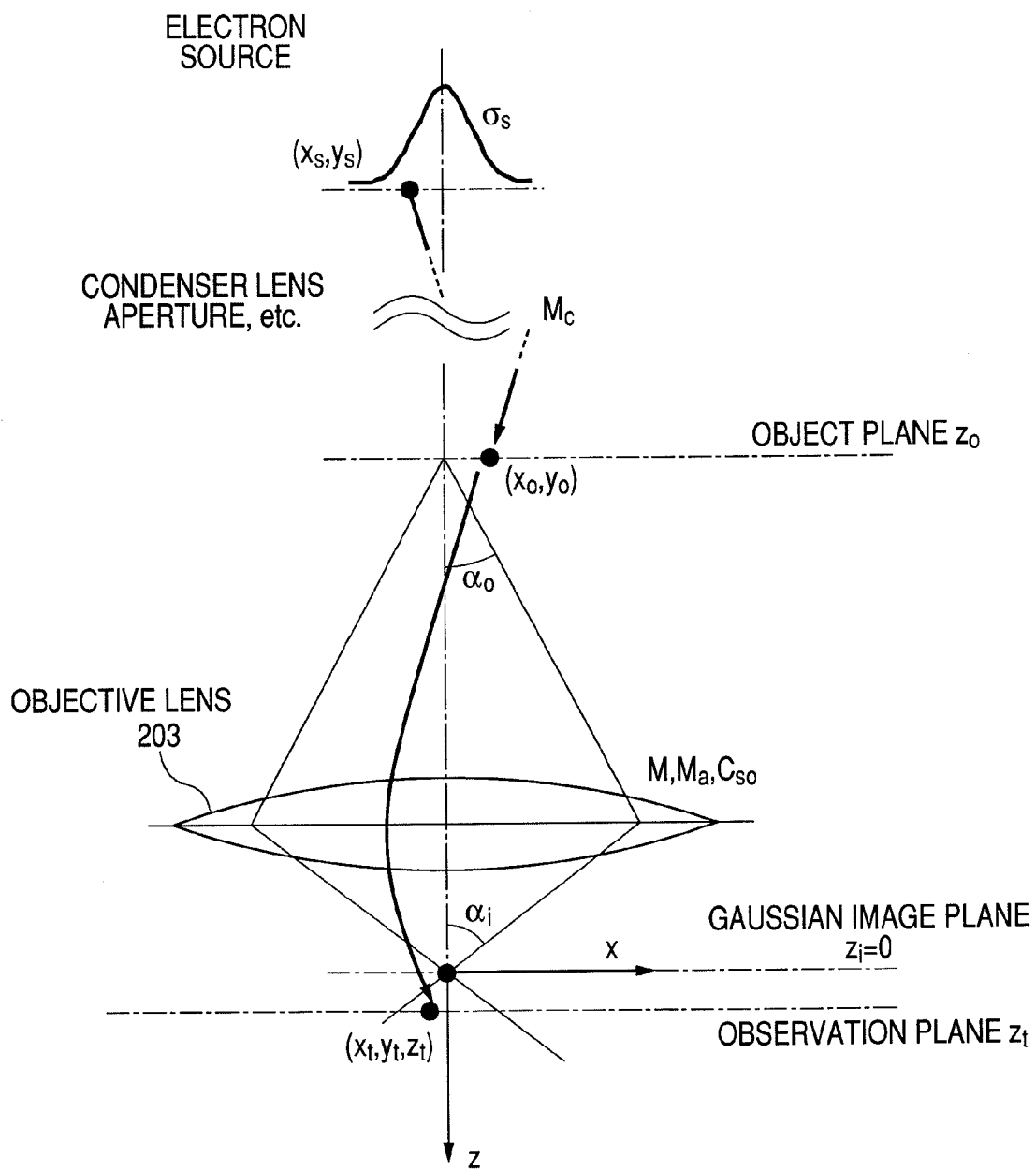
FIG. 11 illustrates the spherical aberration of an electron beam irradiation model.
Figure 12:
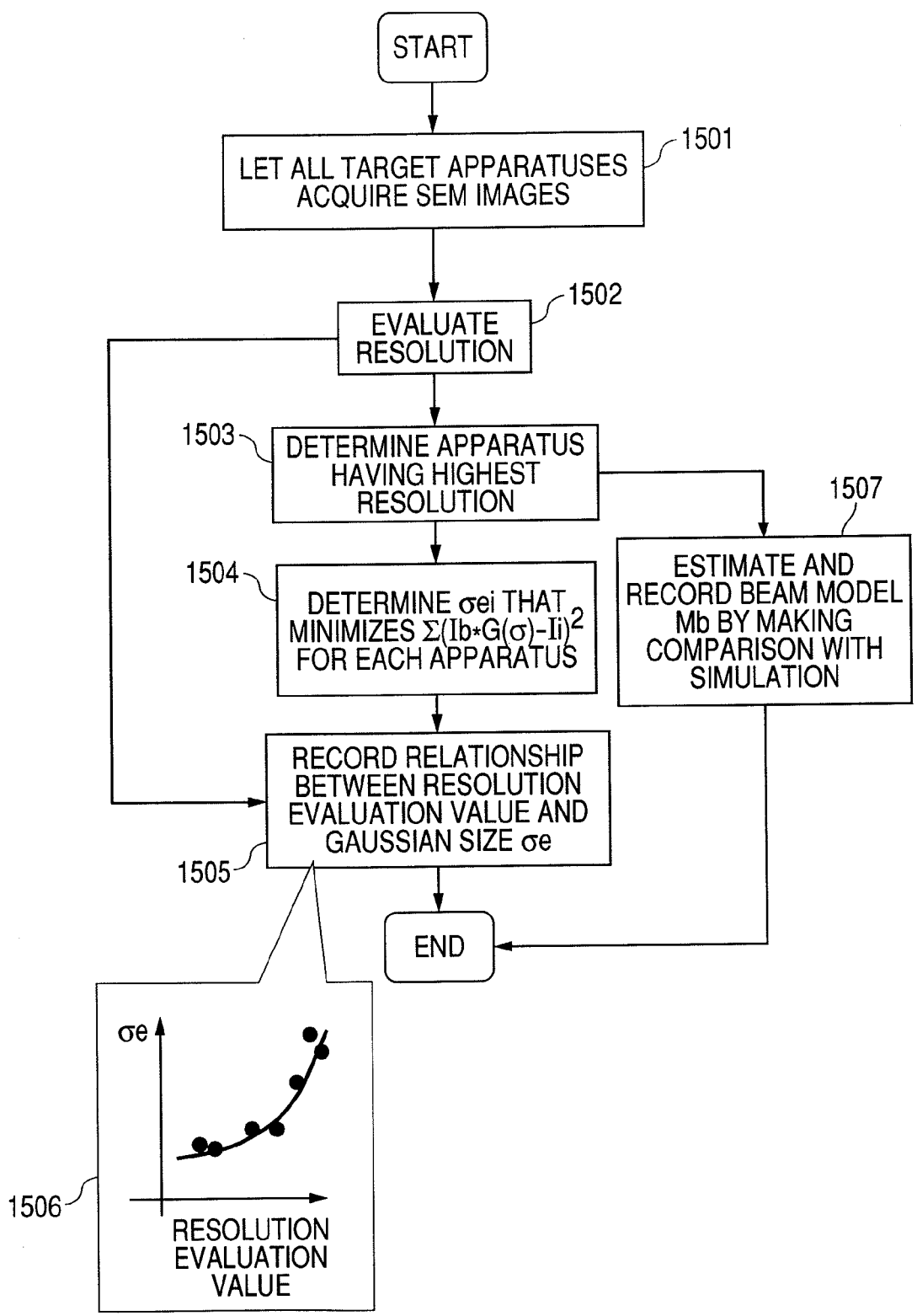
FIG. 12 illustrates a second embodiment of a procedure for compensating for the electron beam resolution difference between SEM measurement apparatuses.

A method for enhancing the accuracy of the third embodiment will now be described with reference to FIG. 11.

The second and third embodiments have been described to explain about a method that performs an electron beam simulation while considering the electron beam divergence half angle α. A fourth embodiment of the present invention additionally takes a spherical aberration into consideration. If there is an aberration during the use of a normal SEM, the orbits of electrons passing outside the objective lens 203 are bent to a greater extent. Therefore, focusing is achieved at different heights depending on the distance from the optical axis. The way in which the electrons are bent can be calculated, for instance, by making an electromagnetic field analysis in accordance with the design information 30 about the electron optics 200 to determine the spherical aberration coefficient. The fourth embodiment performs an electron beam simulation with the electron trajectory changed in accordance with the spherical aberration coefficient. This simulation is described in detail by M. Sato and J. Orloff, "A method for calculating the current density of charged particle beams and the effect of finite source size and spherical and chromatic aberrations on the focusing characteristics," J. Vac. Sci. Technol. B5 (9), September/October 1991 (hereinafter referred to as J. Vac. Sci. Technol. B5 (9)) and P. B. Kenway and G. Cliff, "Electron density distributions in spherically aberrated probes," Inst. Phys. Conf. Ser. No. 68, Chapter 3 1983 (hereinafter referred to as Inst. Phys. Conf. Ser. No. 68). As regards the present embodiment, a typical use of the method disclosed by J. Vac. Sci. Technol. B5 (9) will be described with reference to FIG. 11.

As described in J. Vac. Sci. Technol. B5 (9), the coordinates $(x_t, y_t)$ in the observation plane onto which electrons emitted from point $(x_0, y_0)$ in the object plane of the objective lens in FIG. 11 are projected can be expressed by Equation (4), which uses a spherical aberration coefficient $C_{s0}$ on the object point side of the objective lens.

$$x_t = M\{x_0 + C_{s0}(x_0'^2 + y_0'^2)x_0'\} + z_t \text{Ma} x_0'$$

$$y_t = M\{y_0 + C_{s0}(y_0'^2 + y_0'^2)y_0'\} + z_t \text{Ma} y_0' \qquad \text{Equation (4)}$$

where $x_0'$ and $y_0'$ are derivative values at point $(x_0, y_0)$, which represents the direction of electron incidence, M is a horizontal magnification of the objective lens, and Ma is an angular magnification of the objective lens. Thus, the present invention gives the incident position $(x_0, y_0)$ and angle of electron incidence on the object plane of the objective lens by using random numbers, calculates secondary electrons that generate from the specimen surface in accordance with the given incidence direction and position, repeats the above procedure by using different random numbers, and adds the results to calculate the secondary electron signal. The electron intensity distribution and incidence direction in the object plane of the objective lens should be given while assuming the electron source distribution of the actual apparatus in accordance, for instance, with experiment evaluations and considering the magnification and aperture size of the condenser lens or the like. If, for instance, the electron source distribution is a Gaussian distribution, the distribution in the object plane should be given by using random numbers appropriate for the distribution in compliance with a Gaussian whose variance is changed in accordance with the objective lens magnification. Further, since the incident angle distribution is smaller than the beam divergence half angle at the object point (α0 in FIG. 11), an angle smaller than the beam divergence half angle should be given by using a random number.

The library is created by using the simulation results of the secondary electron signal calculated in the above manner. It goes without saying that the model described in Inst. Phys. Conf. Ser. No. 68 can also be used to perform a similar simulation. After completion of simulation, the same sequence as described in conjunction with the third embodiment should be followed after determining the Gaussian filter for incorporating the apparatus characteristics. When the size of the Gaussian filter obtained in the same manner as in the third embodiment is recorded in the apparatus characteristics database 7 and used when the processing/control section 300 or image processing unit 8 performs a measurement matching process, it is possible to make stable, high-precision measurements.

According to the present embodiment, measurements can be made with increased accuracy when a spherical aberration, which is one of the major SEM aberrations, is taken into consideration. Since the spherical aberration is preset in accordance with the design values, it is possible to make stable, high-speed measurements. Although the present embodiment has been described in relation to the spherical aberration, the same method can also be applied to the other electron optics aberrations.

Fifth Embodiment (Applying Another Method)

Various methods for evaluating the resolution with an actual image have been proposed. For example, the method disclosed by Japanese Patent JP-A No. 142021/2003 (CG method) evaluates the resolution by using the brightness gradient of each local region within an image. Further, an evaluation method based, for instance, on FFT, autocorrelation, and crosscorrelation is disclosed by Proc. SPIE 3998. These methods can make a quantitative evaluation of resolution, but cannot directly reflect evaluation results in an electron beam simulation. A fifth embodiment will now be described as a method for reflecting evaluation values derived from the above evaluations in an electron beam simulation. The method used by the fifth embodiment differs from that is used by the third embodiment, which makes high-precision measurements by performing an electron beam simulation in which the apparatus characteristics are reflected.

The fifth embodiment separately acquires an evaluation value by an existing resolution evaluation method and stores its relationship to the above-mentioned Gaussian filter size. When images placed under various resolution conditions are evaluated in this manner to record the relationship between the resolution evaluation value and Gaussian filter size in the apparatus characteristics database 7, the apparatus characteristics can be subsequently set by the above resolution evaluation method without performing a matching process or an electron beam simulation. As is the case with the third embodiment, all the apparatuses (n units) acquire the SEM image of the reference sample as a tool-tool-disparity evaluation SEM image (step 1501). In this instance, the same sample need not be used for all the apparatuses depending on the employed resolution evaluation method. Next, the image resolution of each apparatus is evaluated (step 1502), and then the apparatus having the highest-resolution is determined (step 1503). Subsequently, the waveform obtained by applying the Gaussian having a standard deviation of σi to the image Ib of the apparatus having the highest resolution is compared with the waveforms Ii of the apparatuses (the symbol i corresponds to the apparatus; e.g., i=1, 2, ... n, i≠b) to determine the value σi=σei that minimizes the error Eb obtained for the waveform of each apparatus from Equation (3).

Consequently, the relationship 1506 between the resolution evaluation value obtained in step 1502 and the Gaussian filter size σei that corresponds to the beam diameter difference between the apparatuses and the apparatus having the highest resolution is recorded in the apparatus characteristics database 7 (step 1505). Meanwhile, the beam model Mb of the apparatus having the highest resolution is estimated and recorded in the apparatus characteristics database 7 (step 1507) as is the case with the third embodiment. The tool-tool-disparity among the other apparatuses can be corrected by using the relationship between the resolution evaluation value and Gaussian filter size and the beam characteristics model of the apparatus having the highest resolution. The resolution of a new apparatus is evaluated by the resolution evaluation method that was used in step 1502. The Gaussian filter size σe for tool-to-tool matching from the relationship 1506 between the resolution evaluation value and Gaussian filter size, the relationship 1506 having been previously determined and recorded. The obtained Gaussian filter and the beam irradiation model Mb of the apparatus having the highest resolution are used to create the library or correct the actual image. As a result, it is possible to make measurements that do not vary from one unit (machine) to another as is the case with the third embodiment.

High sensitivity is often obtained through the use of a sample covered with evaporated gold particles or other special sample depending on the employed resolution evaluation method. In such an instance, an appropriate sample image should be simultaneously acquired under the same conditions at the time of SEM image acquisition. When, in subsequent measurements, the resolution is evaluated with a sample suitable for resolution evaluation and the Gaussian filter size corresponding to the obtained evaluation result is read from the apparatus characteristics database 7, it is possible to set up the apparatus characteristics for measurements. When the above apparatus characteristics evaluation is periodically made and reflected in measurement, it is possible to make stable, high-precision measurements at all times. The frequency of evaluation should be determined depending on the parameter's susceptibility to changes. For example, the evaluation should normally be made at one-week intervals and should be measured without fail when an electron gun chip or other SEM part is replaced.

As described above, the present invention evaluates the SEM resolution in advance, performs an electron beam simulation in which the evaluation results are reflected, and creates the library 3. Since the difference in apparatus characteristics is reflected beforehand in the library, it is possible to reduce the tool-tool-disparity and the measurement error that may be caused by changes with time. The apparatus parameters need not be estimated by the nonlinear least-squares method; therefore, the number of parameters to be estimated can be reduced. When the nonlinear least-squares method is used, the time required for estimation increases with an increase in the number of parameters to be estimated. If similar signal waveforms are given with a certain number of parameter combinations, the results might not converge. If there are a large number of parameters, the estimation accuracy for each parameter may decrease due to the influence of noise, thereby reducing measurement repeatability. Meanwhile, the present invention predetermines the apparatus parameters by a different method. Therefore, the present invention can avoid vagueness in parameter estimation and make stable, high-speed measurements of a plurality of apparatuses for a long period of time.

Sixth Embodiment (Detector Characteristics)

A sixth embodiment, which relates to a method for providing enhanced measurement stability by predetermining the gain and offset of a detector, will now be described.

Figure 13:
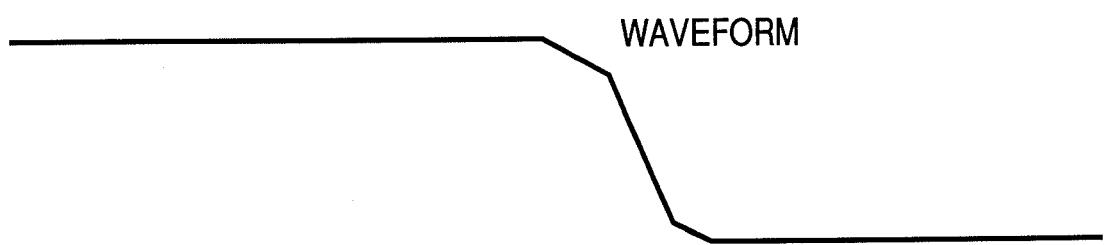
FIG. 13 shows an embodiment of a first sample for measuring a plurality of apparatus characteristics.
Figure 13:
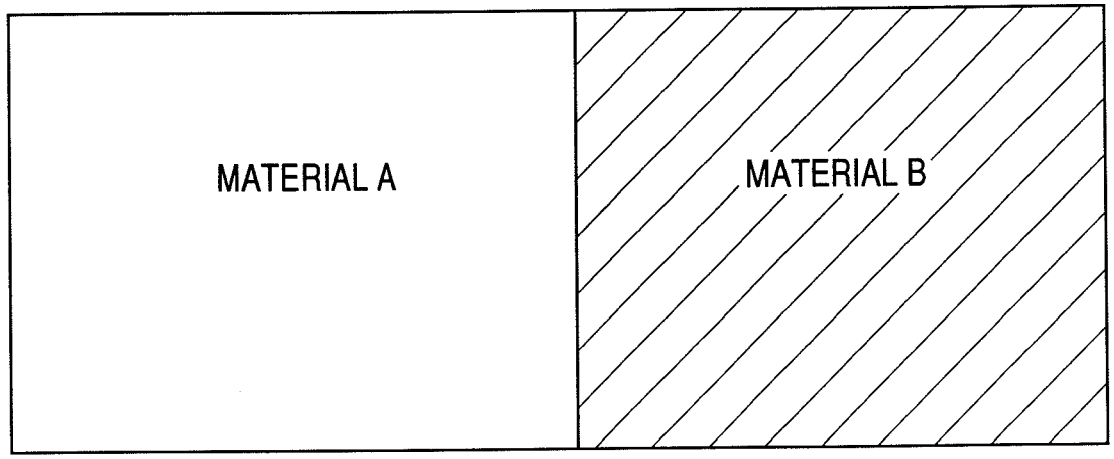
Figure 14:
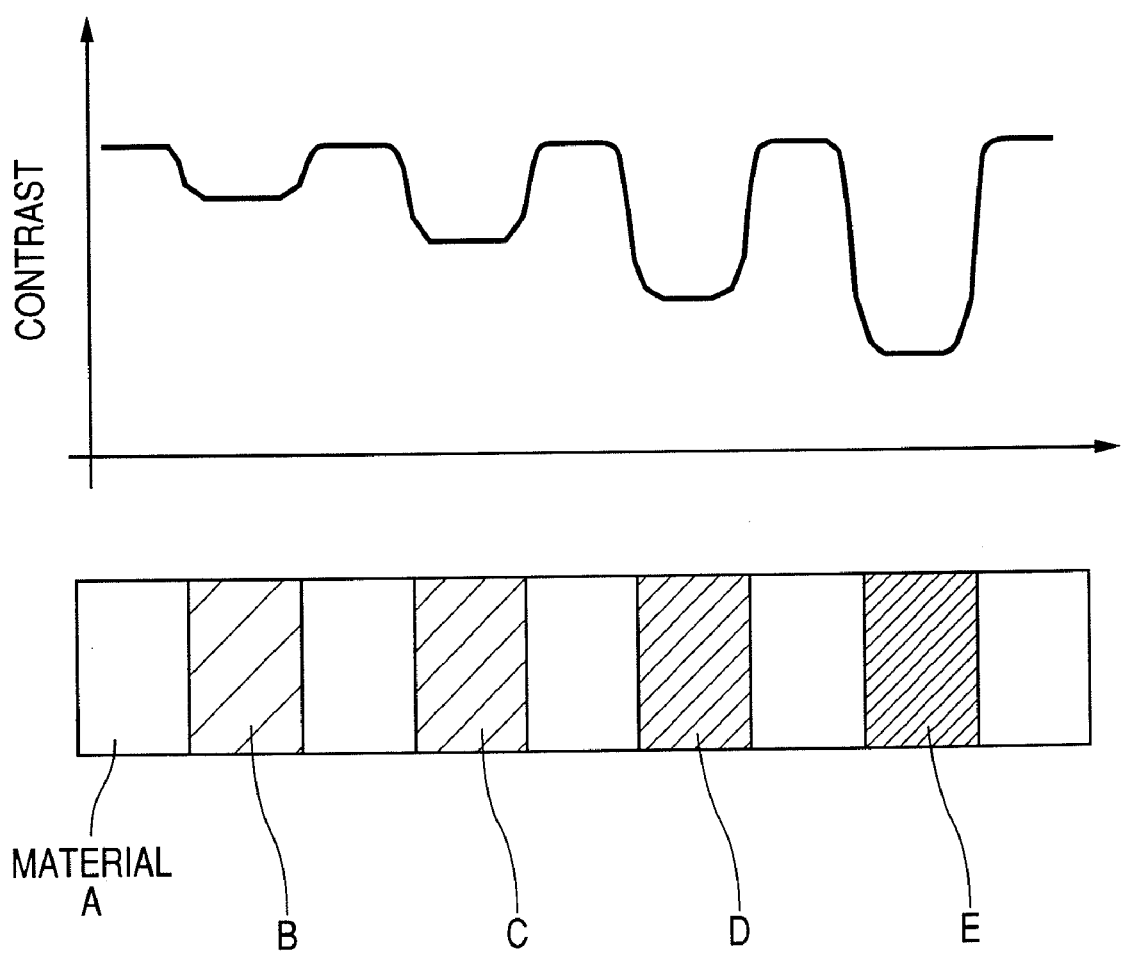
FIG. 14 shows an embodiment of a second sample for measuring a plurality of apparatus characteristics.

The present invention operates so that, for instance, the simulation unit 9 sets the gain and offset, for instance, of the secondary electron detector by using the contrasts of two or more materials in sample images being already-known two or more different materials acquired in the image database 5. Appropriate image processing conditions are set up before acquiring a measurement image, and the sample images being already-known two or more different materials are acquired before acquiring an actual image. In this instance, the sample surface is sufficiently flat and large. The sample images may be separately acquired or only one image may be used if there is a region in which two materials are adjacent to each other as shown in FIG. 13. The resulting signal waveforms are examined. The average brightness of a region in which a waveform is stable is calculated and the gain and offset are determined in accordance with the relationship between the average brightness and the signal amount of an electron beam simulation image in each region. If the detector characteristics are linear, the stable estimation of the gain and offset can be sufficiently achieved when two different materials are involved. If, on the other hand, the detector characteristics are nonlinear, correction between the simulation and actual signal amounts should be performed by using a plurality of materials that differ in contrast as indicated in FIG. 14. For correction purposes, the gamma correction technique, which is generally used for image gradation correction, may be used. Further, when the surface irregularities of a sample having material boundaries as shown in FIG. 13 or 14 are smoothed out by chemical mechanical polishing or other similar means, it is possible to eliminate SEM image edge effects from the boundaries. Acquiring such an image makes it possible to evaluate the waveforms of the boundaries, avert the influence of a pattern shape, and evaluate the changes in the beam shape and resolution.

As described above, the present invention calibrates the gain and offset of the detector in accordance with an actual image, and performs gradation conversion of electron beam simulation results while considering the calibration results. Consequently, the parameters need not be estimated by the nonlinear least-squares method, and the number of parameters to be estimated can be reduced. When the nonlinear least-squares method is used, the time required for estimation increases with an increase in the number of parameters to be estimated. If similar signal waveforms are given with a certain number of parameter combinations, the results might not converge. If there are a large number of parameters, the estimation accuracy for each parameter may decrease due to the influence of noise, thereby reducing measurement repeatability. Meanwhile, the present invention predetermines the apparatus parameters by a different method. Therefore, the present invention can avoid vagueness in parameter estimation and make consistent, high-speed measurements.

Seventh Embodiment (Stereo)

Figure 15A:
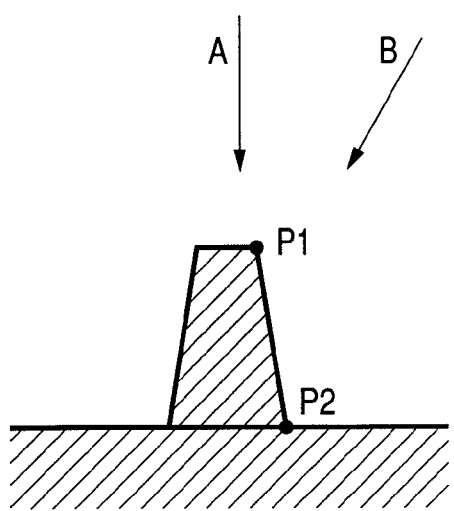
FIG. 15A shows a pattern that is placed in a horizontal position and irradiated with a vertical electron beam (A) and an oblique electron beam (B).
Figure 15C:
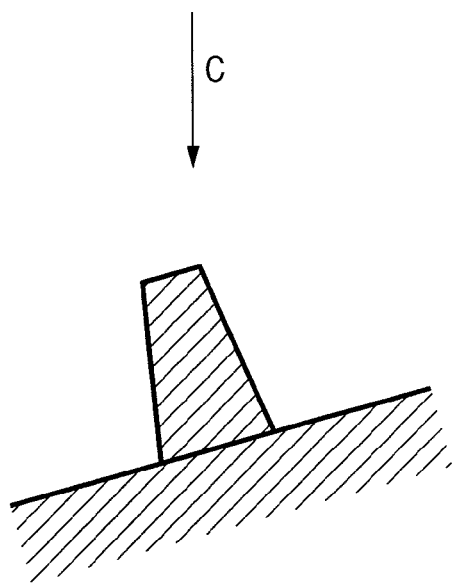
FIG. 15C shows an SEM image that is obtained when the pattern shown in FIG. 15A is irradiated with a vertical electron beam (A).
Figure 15B:
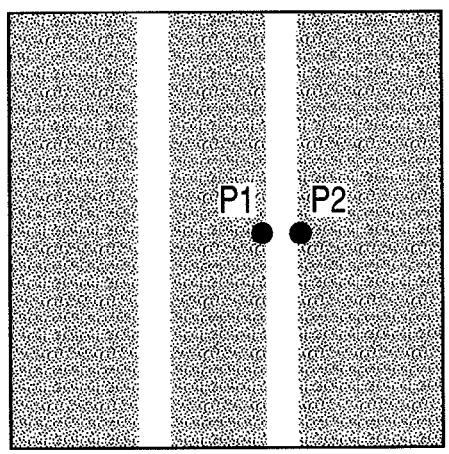
FIG. 15B shows a pattern that is obliquely placed (tilted) and irradiated with a vertical electron beam (C).
Figure 15D:
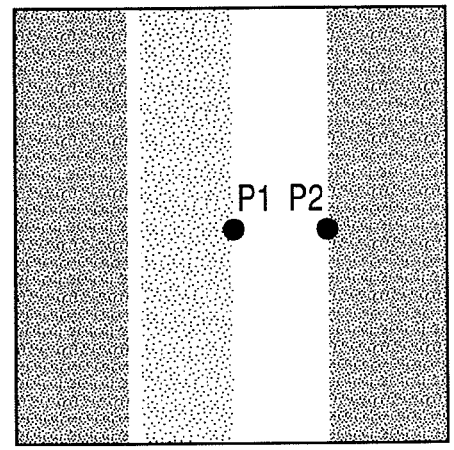
FIG. 15D shows an SEM image that is obtained when the pattern shown in FIG. 15A is irradiated with an oblique electron beam (B) or when the pattern shown in FIG. 15B is irradiated with a vertical electron beam (C).

A method for acquiring more accurate three-dimensional shape information, which is based on the method described above, will now be described with reference to FIGS. 15A to 15D. A stereo method detects corresponding points within two images that are picked up from different view points, and makes three-dimensional measurements of the images in accordance with the amount of positional displacement between the corresponding points. FIGS. 15A to 15D illustrate an embodiment of the SEM image acquisition method to which the stereo method is to be applied. The normal CD-SEM image (image A) shown in FIG. 15B is picked up with an electron beam that is oriented in direction A as shown in FIG. 15A. CD-SEM images B and C, which are shown in FIG. 15D, can be picked up from different view points by tilting an electron beam (B) as shown in FIG. 15A or by tilting the stage without tilting the electron beam (C) as shown in FIG. 15C. When points P1 and P2, which are on the sample, are accurately detected from the images, the height difference between points P1 and P2 can be measured from the positional relationship between points P1 and P2. In reality, however, it is difficult to accurately locate the above points within the images. The reason is that it is difficult to accurately determine the edge positions because the SEM signal waveform varies with the target shape and beam irradiation direction as is the case with examples indicated in Proc. SPIE 4689 and Proc. SPIE 5038. Further, when image qualities such as resolution differ between stereo images, the edge position detection accuracy varies, thereby causing a problem.

Figure 16:
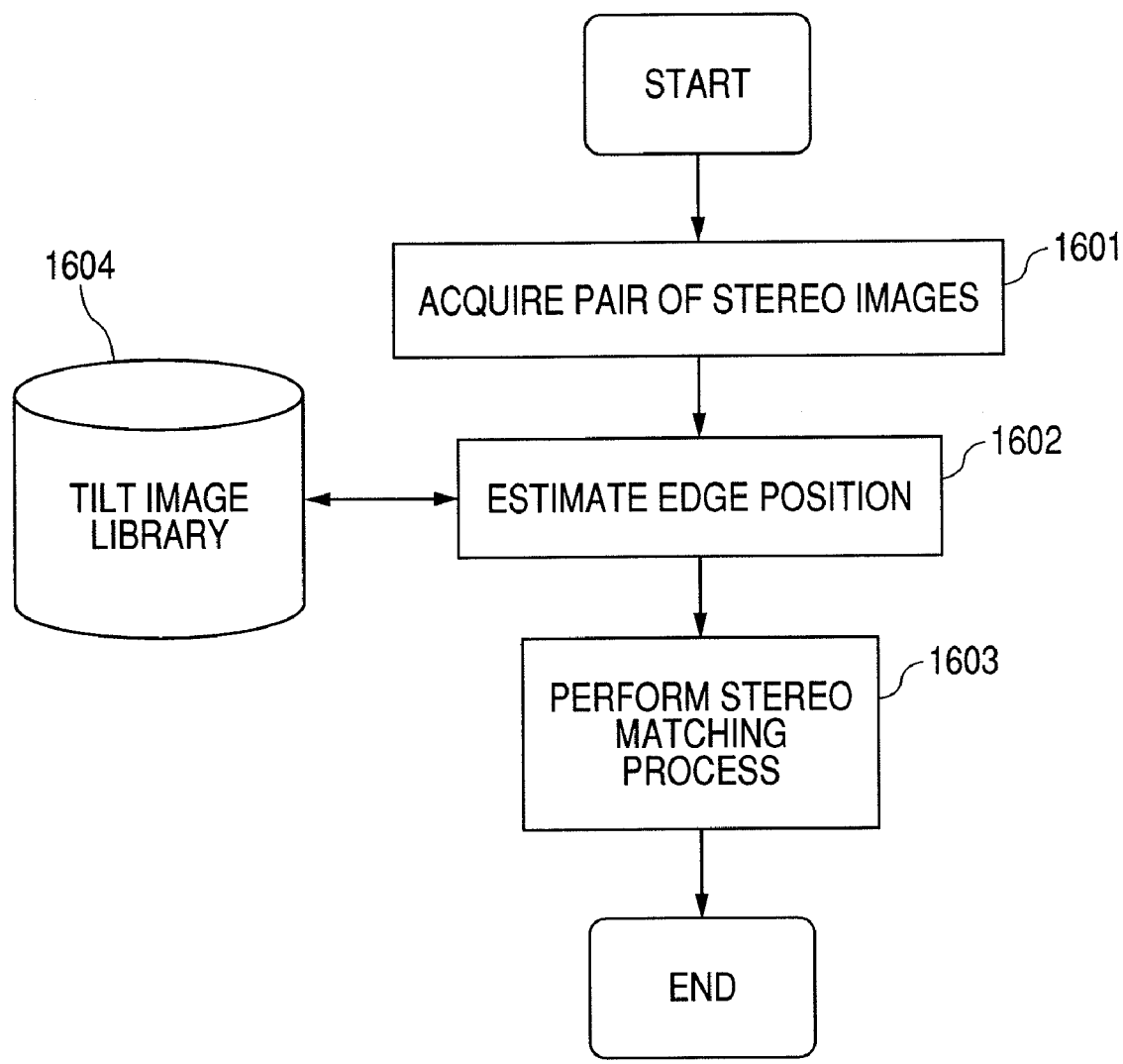
FIG. 16 illustrates a first embodiment of a procedure for measuring a three-dimensional shape by using images obtained from a plurality of observation directions.

Thus, the present invention creates a tilt image library 1604 and causes the processing/control section 300 or image processing unit 8 to compare the stereo images with the library. The procedure is indicated in FIG. 16. First of all, a pair of stereo SEM images are picked up from incident angles of two or more different electron beams (step 1601). An image quality change caused by tilting, for example, the amount of a resolution change, is stored in advance in the apparatus characteristics database 6 in accordance with a design value or measured value as is the case with the first to fifth embodiments, and reflected in library creation or matching. Next, the pattern edge position is estimated on an individual image by making comparison with the library (which contains position coordinates) 1604 that is created at the same tilt angle as the image acquisition conditions (step 1602). As is the case with the first to fifth embodiments, this comparison makes it possible to accurately detect the edge positions without regard to the target shape or apparatus characteristics. Since the incident angles (tilt angles) of two or more different electron beams are known, the pattern height, which relates to the three-dimensional shape of the measurement target pattern, can be estimated by performing a stereo matching process on the results, that is, by calculating the positional relationship between the obtained edge positions (step 1603). When the present invention is applied to a tilt image as described above, it is possible to make accurate height measurements although conventional SEM image processing methods cannot make height measurements with sufficient accuracy.

Eighth Embodiment (Stereo)

Figure 17A:
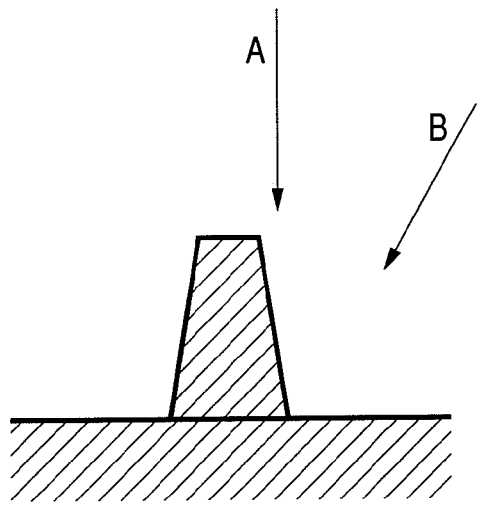
FIG. 17A shows a cross-sectional view of a pattern and the directions of electron beam incidence (tilt angles).
Figure 17B:
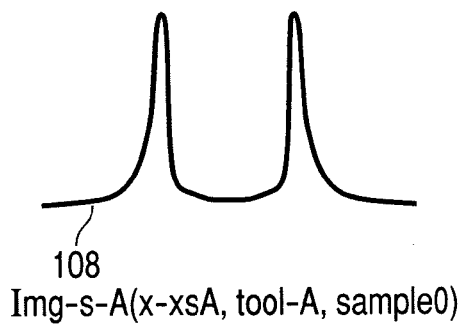
FIG. 17B shows the result of a simulation that is performed to determine an SEM image signal prevailing when an electron beam is irradiated on the pattern shown in FIG. 17A at a tilt angle of A.
Figure 17C:
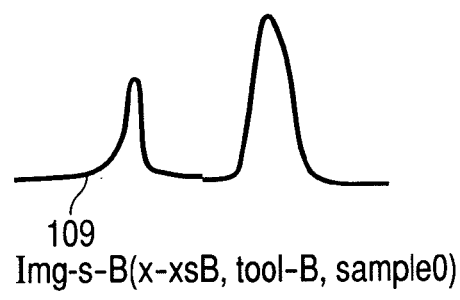
FIG. 17C shows the result of a simulation that is performed to determine an SEM image signal prevailing when an electron beam is irradiated on the pattern shown in FIG. 17A at a tilt angle of B.
Figure 17D:
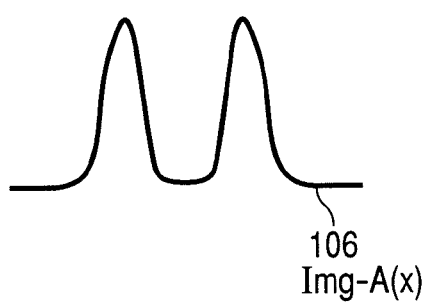
FIG. 17D shows an SEM image signal that is obtained when an electron beam is irradiated on the pattern shown in FIG. 17A at a tilt angle of A.
Figure 17E:
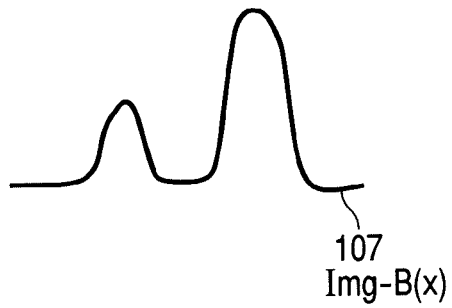
FIG. 17E shows an SEM image signal that is obtained when an electron beam is irradiated on the pattern shown in FIG. 17A at a tilt angle of B.

An eighth embodiment, which relates to a method for estimating the three-dimensional shape of the target pattern from a plurality of images obtained at different angles, will now be described with reference to FIGS. 17A to 17E. First of all, a library in which beam characteristics are reflected is created for each set of image acquisition conditions (electron beam landing energy (accelerating voltage), beam shape, pixel size (image acquisition magnification), etc.) as is the case with the seventh embodiment. It is assumed that images actually picked up at tilt angles A and B, which are shown in FIG. 17A, are image Img-A(x) 106 and image Img-B(x) 107 as shown in FIGS. 17D and 17E. It is also assumed that simulation images of a certain sample shape (sample 0) obtained at tilt angles of A and B are image Img-s-A (x, tool-A, sample 0) 108 and image Img-s-B (x, tool-B, sample 0) 109 as shown in FIGS. 17B and 17C. The matching error Estereo between the simulation images and actual images is defined by Equation (5).

$$\text{Estereo} = \Sigma[\{\text{Img-s-}A(x\text{-}(xs\text{-}A), \text{tool-}A, \text{sample }0) - \text{Img-}A(x)\}^2 + \{\text{Img-s-}B(x\text{-}(xs\text{-}B), \text{tool-}B, \text{sample }0) - \text{Img-}B(x)^2\}] \quad \text{Equation (5)}$$

The present embodiment uses the nonlinear least-squares method to determine (xs-A), (xs-B), and (sample 0) that minimize the error Estereo, thereby making it possible to estimate the target shape parameters for all the stereo images that are sufficiently similar to the simulation results. When images are picked up from different directions as described above, the target shape parameters can be estimated with high accuracy. Here, apparatus characteristics parameters (tool-A) and (tool-B) are preset by the method described in conjunction with the first to fifth embodiments; therefore, it is not necessary to determine the apparatus characteristics parameters at the time of measurement. Further, since tilt angles A and B are known, the three-dimensional shape corresponding to the sample parameters that minimize the error Estereo is measured as a measurement target pattern shape. Although the present embodiment assumes that two images are used, three or more images obtained at different angles may be used alternatively.

The use of the method described above makes it possible to make accurate pattern shape measurements without regard to the target shape or apparatus characteristics as is the case with the first to fifth embodiments. When the present invention is applied to a tilt image as described above, it is possible to make accurate height measurements although conventional SEM image processing methods cannot make height measurements with sufficient accuracy.

The pattern measurement technology according to the present invention can be applied to any target as far as its image can be acquired by an electron microscope. The present invention can be used to measure MEMS and minute industrial parts as well as semiconductor patterns.

The present invention may be embodied in other specific forms without departing from the spirit or essential characteristics thereof. The embodiments described above are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for measuring a measurement target pattern with an electron microscope to acquire an actual electron microscope image of the measurement target pattern under image acquisition conditions and estimate shape of the measurement target pattern by using the acquired actual electron microscope image, the method comprising:

a measurement recipe creation step of obtaining pattern shape information by modeling approximate shapes of various target patterns in numerical data in advance, which are obtained by varying dimensions in a predetermined predicted variation range;

a library creation step of creating first simulated waveforms of electron microscope signals concerning various target pattern shapes by performing electron beam simulations for the various target pattern shapes within the predicted variation range, the electron beam simulations representing characteristics of an electron microscope, including electron optics resolution, beam divergence half angle and aberration coefficients, and image acquisition condition imposed by the electron microscope, and storing a combination of the created first simulated waveforms of the electron microscope signals and the pattern shape information, which correspond to the first simulated waveforms and are obtained in the measurement recipe creation step, as a library; and a measurement step of acquiring an actual electron microscope image of a measurement target pattern with the electron microscope which is adjusted in focus and astigmatism and selecting a first simulated waveform or a second simulated waveform which is most similar to the acquired actual electron microscope image by comparing the acquired actual electron microscope image with the first simulated waveforms of the electron microscope signals created in the library creation step, or second simulated waveforms which are created from the first simulated waveforms, and estimating the shape of the measurement target pattern from the pattern shape information that corresponds to the selected first simulated waveform or second simulated waveform and is used in the library creation step, wherein the library creation step includes the steps of:

calculating a best focus position by using simulation images for each of the target pattern shapes in the same evaluation method as with an actual electron microscope, in advance; and reflecting the calculated best focus position in the electron beam simulation as an image acquisition condition imposed by the electron microscope.

2. The method according to claim 1, wherein in the library creation step, the apparatus characteristic of the electron microscope is any one of an electron optics resolution, a beam shape, a beam divergence half angle or aberration coefficients, or a combination of two or more of the electron optics resolution, the beam shape, the beam divergence half angle and the aberration coefficients.

3. The method according to claim 2, wherein in the library creation step, the any one of the electron optics resolution, the beam shape, the beam divergence halt angle or the aberration coefficients, or the combination of two or more of the electron optics resolution, the beam shape, the beam divergence half angle and the aberration coefficients being the apparatus characteristic of the electron microscope reflected in the electron beam simulation, is determined by using design information about the electron microscope.

4. The method according to claim 2, wherein in the library creation step, the any one of the electron optics resolution, the beam shape, the beam divergence half angle or the aberration coefficients, or the combination of two or more of the electron optics resolution, the beam shape, the beam divergence half angle and the aberration coefficients being the apparatus characteristic of the electron microscope reflected in the electron beam simulation, is determined based on measurement results measured by a measurement means.

5. The method according to claim 1, wherein the library creation step includes the steps of:

storing the apparatus characteristic of the electron microscope for each apparatus of the electron microscope; and reflecting the apparatus characteristic in the electron beam simulation, which is obtained by reading the apparatus characteristic stored for each apparatus of the electron microscope when the first simulated waveform is to be created.

6. The method according to claim 1, wherein the library creation step includes the steps of:
- storing the apparatus characteristic of the electron microscope for each set of the image acquisition conditions including at least electron beam landing energy and pixel size; and
- reflecting the apparatus characteristic in the electron beam simulation, which is obtained by reading the apparatus characteristic stored for each set of the image acquisition conditions when the first simulated waveform is to be created.

7. The method according to claim 1, wherein in the library creation step, the created first simulated waveforms of the electron microscope signals stored in combination with the pattern shape information is reflected by a tool-tool-disparity information with a second electron microscope.

8. The method according to claim 7, wherein said tool-tool-disparity information is calculated from plural images which are obtained from the electron microscope and the second electron microscope by imaging a same sample.

9. The method according to claim 8, wherein said tool-tool-disparity information includes differences in resolution between the electron microscope and the second electron microscope.

10. The method according to claim 8, wherein said tool-tool-disparity information is renewed by new tool-tool-disparity information calculated from plural images obtained from the electron microscope and the second electron microscope by imaging the same sample with an interval depending on a frequency of variation.

11. A method for measuring a measurement target pattern with an electron microscope to acquire actual electron microscope images of the measurement target pattern with electron beams at two or more different incident angles under image acquisition conditions and estimate the three-dimensional shape of the measurement target pattern by using the acquired two or more actual electron microscope images, the method comprising:
- a measurement recipe creation step of obtaining pattern shape information by modeling approximate shapes of various target patterns in numerical data in advance, which are obtained by varying dimensions in a predetermined predicted variation range;
- a library creation step of creating a group of first simulated waveforms of electron microscope signals obtained by irradiating the various target pattern shapes with the electron beams at the two or more different incident angles by performing electron beam simulations on the various target pattern shapes within the predicted variation range, the electron beam simulations representing characteristics of an electron microscope, including electron optics resolution, beam divergence half angle and aberration coefficients, and image acquisition conditions imposed by the electron microscope, including conditions for emitting electron beams at the two or more different incident angles, and storing a combination of the created group of the two or more first simulated waveforms of the electron microscope signals and the pattern shape information, which corresponds to the created group of the first simulated waveforms and is obtained in the measurement recipe creation step, as a library; and
- a measurement step of acquiring an actual electron microscope image of a measurement target pattern with the electron microscope which is adjusted in focus and astigmatism and comparing the acquired two or more actual electron microscope images with the group of the first simulated waveforms created in the library creation step or a group of second simulated waveforms, which are created from the group of the first simulated waveforms, and measuring the three-dimensional shape of the measurement target pattern by selecting the pattern shape information that minimizes total errors between the two or more actual electron microscope images and the group of the first simulated waveforms or the group of the second simulated waveforms, wherein the library creation step includes the steps of:
- calculating a best focus position by using simulation images for each of the target pattern shapes in the same evaluation method as with an actual electron microscope, in advance; and
- reflecting the calculated best focus position in the electron beam simulation as an image acquisition condition imposed by the electron microscope.

12. A method for measuring a measurement target pattern with an electron microscope to acquire actual electron microscope images of the measurement target pattern with electron beams at two or more different incident angles under image acquisition conditions and estimate the three-dimensional shape of the measurement target pattern by using the acquired two or more actual electron microscope images, the method comprising:
- a measurement recipe creation step of obtaining pattern shape information by modeling approximate shapes of various target patterns in numerical data in advance, which are obtained by varying dimensions in a predetermined predicted variation range;
- a library creation step of creating a group of first simulated waveforms of electron microscope signals obtained by irradiating the various target pattern shapes with the electron beams at the two or more different incident angles by performing electron beam simulations on the various target pattern shapes within the predicted variation range, the electron beam simulations representing characteristics of an electron microscope, including electron optics resolution, beam divergence half angle and aberration coefficients, and image acquisition conditions imposed by the electron microscope, including conditions for emitting electron beams at the two or more different incident angles, and storing a combination of the created group of the two or more first simulated waveforms of the electron microscope signals and the pattern shape information, which corresponds to the created group of the first simulated waveforms and is obtained in the measurement recipe creation step, as a library; and
- a measurement step of acquiring an actual electron microscope image of a measurement target pattern with the electron microscope which is adjusted in focus and astigmatism and comparing the acquired two or more actual electron microscope images with the group of the first simulated waveforms created in the library creation step or a group of second simulated waveforms, which are created from the group of the first simulated waveforms, and measuring the three-dimensional shape of the measurement target pattern by selecting the pattern shape information that minimizes total errors between the two or more actual electron microscope images and the group of the first simulated waveforms or the group of the second simulated waveforms, wherein the library creation step includes the steps of:
- calculating a best focus position by using simulation images for each of the target pattern shapes in the same evaluation method as with an actual electron microscope, in advance; and reflecting the calculated best focus position in the electron beam simulation as an image acquisition condition imposed by the electron microscope.

13. A method of measuring a target pattern and estimating a shape of the target pattern comprising the steps of:

acquiring a plurality of images of the target pattern using a plurality of different apparatuses;

determining which apparatus has the highest resolution, based on evaluation of the acquired images;

selecting an image acquired by the highest resolution apparatus and designating the selected image as an actual electron microscope image of the target pattern;

creating a measurement recipe creation by obtaining pattern shape information and numerically modeling, in advance, approximate shapes of various target patterns obtained by varying dimensions in a predetermined predicted variation range;

creating a library of first simulated waveforms by:

performing electron beam simulations for various target pattern shapes within the predicted variation range, the electron beam simulations representing characteristics of an electron microscope, including electron optics resolution, beam divergence half angle and aberration coefficients, and image acquisition condition imposed by the electron microscope, and storing a combination of the created first simulated waveforms of the electron microscope signals and the pattern shape information corresponding to the first simulated waveforms, as a library;

adjusting focus and astigmatism of the actual electron microscope image of the target pattern;

comparing the acquired actual electron microscope image with either the first simulated waveforms, or second simulated waveforms which are created from the first simulated waveforms;

selecting a first simulated waveform or a second simulated waveform which is most similar to the acquired actual electron microscope image; and estimating the shape of the measurement target pattern from the pattern shape information that corresponds to the selected first simulated waveform or second simulated waveform and is used in creating the library, wherein the step of creating a library further comprises the steps of:

calculating a best focus position by using simulation images for each of the target pattern shapes in the same evaluation method as with an actual electron microscope, in advance, and reflecting the calculated best focus position in the electron beam simulation as an image acquisition condition imposed by the electron microscope.

* * * * *